United States Patent
Ma et al.

(10) Patent No.: US 6,355,620 B1
(45) Date of Patent: Mar. 12, 2002

(54) C-2 MODIFIED ERYTHROMYCIN DERIVATIVES

(75) Inventors: Zhenkun Ma, Gurnee; Yat Sun Or, Libertyville; Ly Tam Phan; Suoming Zhang, both of Park City; Richard F. Clark, Mundelein, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/312,517

(22) Filed: May 14, 1999

(51) Int. Cl.⁷ .......................... A61K 31/70; C07H 1/00; C07H 17/08
(52) U.S. Cl. .......................... 514/29; 536/7.2; 536/7.4; 536/18.5
(58) Field of Search .................. 536/7.2, 7.4, 18.5; 514/29

(56) References Cited

U.S. PATENT DOCUMENTS 5,747,467 A    5/1998    Agouridas et al. ............ 514/29

FOREIGN PATENT DOCUMENTS

| EP | 0559896 | 11/1991 |
| EP | 0638585 | 11/1996 |

*Primary Examiner*—Elli Peselev
(74) *Attorney, Agent, or Firm*—Mona Anand; Dugal S. Sickert

(57) ABSTRACT

A compound having the formula selected from the group consisting of
a compound of formula I (I)

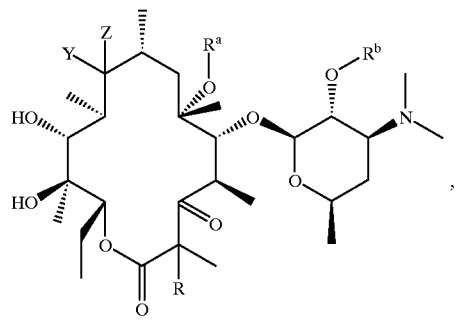

a compound of formula II (II)

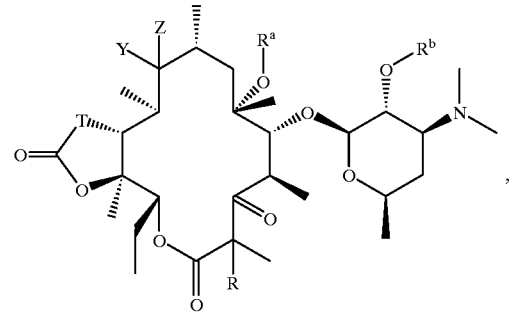

a compound of formula III

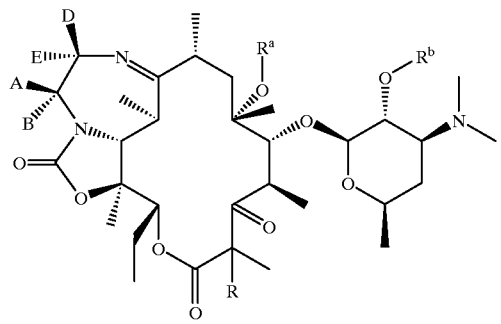

as well as and pharmaceutically acceptable salts, esters, solvates, metabolites, and prodrugs thereof, are useful in treating bacterial infections. Also provided are pharmaceutically acceptable compositions, methods of treating bacterial infections, and processes for the preparation of the compounds.

13 Claims, No Drawings

C-2 MODIFIED ERYTHROMYCIN DERIVATIVES

TECHNICAL FIELD

The present invention relates to semisynthetic macrolides and compositions which are antibacterial agents, processes for making the compounds, synthetic intermediates employed in the processes, and methods for treatment and prevention of bacterial infections in a mammal.

BACKGROUND OF THE INVENTION

Erythromycins A through D, represented by formula (E),

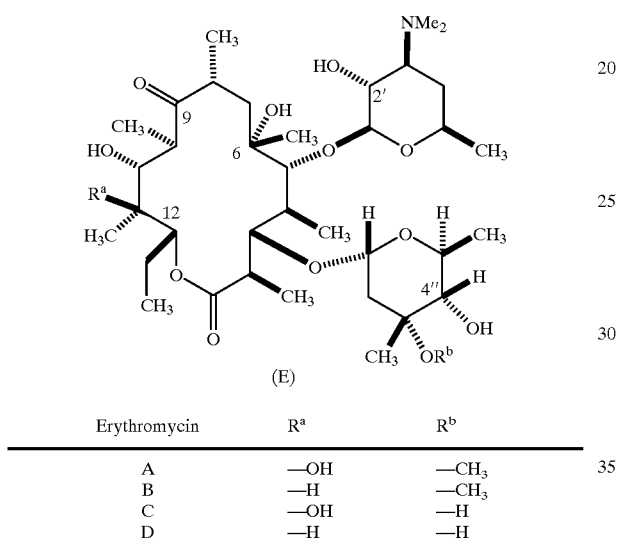

(E)

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents which are widely used to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which have improved antibacterial activity, less potential for developing resistance, the desired Gram-negative activity, or unexpected selectivity against target microorganisms. Consequently, numerous investigators have prepared chemical derivatives of erythromycin in an attempt to obtain analogs having modified or improved profiles of antibiotic activity.

Kashimura, et al. have disclosed 6-O-methylerythromycin derivatives having a tricyclic basic nuclear structure in European Application 559896, published Nov. 11, 1991, and Asaka, et al. have disclosed 5-O-desoaminylerythronolide derivatives 1991, and Asaka, et al. have disclosed 5-O-desoaminylerythronolide derivatives containing a tricyclic carbamate structure in PCT Application WO 93/21200, published Apr. 22, 1992.

SUMMARY OF THE INVENTION

In one embodiment of the present invention are compounds selected from the group consisting of a compound of formula (I)

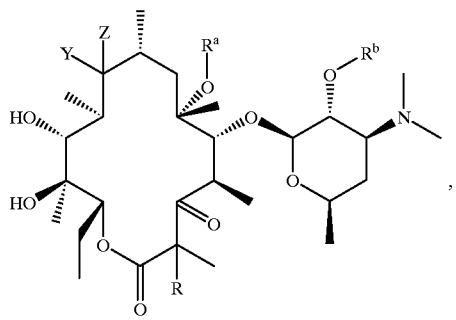

(I)

a compound of formula (II)

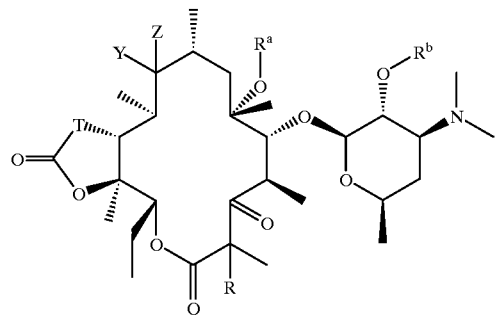

(II)

and
a compound of formula (III)

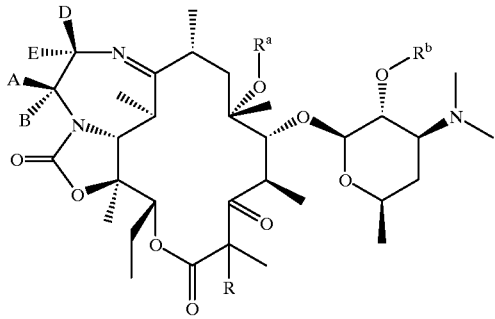

(III)

wherein, in formulas (I)–(III),
Y and Z together are selected from the group consisting of
(1) oxo,
(2) =N—OH,
(3) =N—OR$^1$ wherein R$^1$ is selected from the group consisting of
  (a) —C$_1$–C$_{12}$-alkyl,
  (b) —C$_1$–C$_{12}$-alkyl substituted with aryl,
  (c) —C$_1$–C$_{12}$-alkyl substituted with substituted aryl,
  (d) —C$_1$–C$_{12}$-alkyl substituted with heteroaryl,
  (e) —C$_1$–C$_{12}$-alkyl substituted with substituted heteroaryl,
  (f) —C$_3$–C$_{12}$-cycloalkyl,
  (g) —Si(R$^2$)(R$^3$)(R$^4$), wherein R$^2$, R$^3$, and R$^4$, are each independently —C$_1$–C$_{12}$— alkyl or aryl, and (h) —$(CH_2)_nNR^5R^6$ wherein n is two to six, and $R^5$ and $R^6$ are independently selected from the group consisting of
  (i) hydrogen,
  (ii) —$C_1$–$C_{12}$-alkyl,
  (iii) —$C_1$–$C_{12}$-alkyl substituted with aryl,
  (iv) —$C_1$–$C_{12}$-alkyl substituted with substituted aryl,
  (v) —$C_1$–$C_{12}$-alkyl substituted with heteroaryl, and
  (vi) —$C_1$–$C_{12}$-alkyl substituted with substituted heteroaryl,
  or
  $R^5$ and $R^6$ taken together with the atom to which they are attached are $C_3$–$C_{12}$-heterocycloalkyl,
and
(4) =N—$OC(R^7)(R^8)$(—$OR^1$), wherein $R^1$ is defined above, and $R^7$ and $R^8$ are independently selected from the group consisting of
  (i) hydrogen,
  (ii) —$C_1$–$C_{12}$-alkyl,
  (iii) —$C_1$–$C_{12}$-alkyl substituted with aryl,
  (iv) —$C_1$–$C_{12}$-alkyl substituted with substituted aryl,
  (v) —$C_1$–$C_{12}$-alkyl substituted with heteroaryl, and
  (vi) —$C_1$–$C_{12}$-alkyl substituted with substituted heteroaryl,
  or
  $R^7$ and $R^8$ taken together with the atom to which they are attached are $C_3$–$C_{12}$-cycloalkyl, or
one of Y and Z is hydrogen, and the other is selected from the group consisting of
  (1) hydrogen,
  (2) hydroxy,
  (3) —$OR^1$ wherein $R^1$ is defined above, and
  (4) —$NR^5R^6$ wherein $R^5$ and $R^6$ are defined above;
T is selected from the group consisting of
  (1) —O—,
  (2) —NH—, and
  (3) —$N(W(R^g))$— wherein W is absent or selected from the group consisting of
    (a) —O—,
    (b) —$(CH_2)_p$— wherein p is one to six, and
    (c) —NH—,
  and
  $R^g$ is selected from the group consisting of
    (a) hydrogen,
    (b) —$C_3$–$C_7$-cycloalkyl,
    (c) aryl,
    (d) substituted aryl,
    (e) heteroaryl,
    (f) substituted heteroaryl,
    (g) —$C_1$–$C_6$-alkyl,
    (h) —$NR^5R^6$ wherein $R^5$ and $R^6$ are defined above, and
    (i) —$C_1$–$C_6$-alkyl substituted with one or more substituents independently selected from the group consisting of
      (i) aryl,
      (ii) substituted aryl,
      (iii) heteroaryl,
      (iv) substituted heteroaryl,
      (v) hydroxy,
      (vi) —$OR^1$, and
      (vii) —$NR^5R^6$ wherein $R^5$ and $R^6$ are defined above;
$R^a$ is selected from the group consisting of
  (1) —$C_1$–$C_{10}$-alkyl optionally substituted with one or more substituents independently selected from the group consisting of
    (a) halogen,
    (b) hydroxy,
    (c) —$OR^1$,
    (d) oxo,
    (e) —$NR^5R^6$ wherein $R^5$ and $R^6$ are defined above,
    (f) —$CO_2R^1$ wherein $R^1$ is defined above,
    (g) —$C(O)NR^5R^6$ wherein $R^5$ and $R^6$ are defined above,
    (h) =N—$OR^1$ wherein $R^1$ is defined above,
    (i) cyano,
    (j) —$S(O)_qR^1$ wherein $R^1$ is defined above and q is zero to two,
    (k) aryl,
    (l) substituted aryl,
    (m) heteroaryl,
    (n) substituted heteroaryl,
    (o) heterocycloalkyl,
    (p) substituted heterocycloalkyl,
    (q) —$NHC(O)R^1$ wherein $R^1$ is defined above,
    (r) —$NHC(O)NR^5R^6$ wherein $R^5$ and $R^6$ are defined above,
    (s) =$NNR^5R^6$ wherein $R^5$ and $R^6$ are defined above,
    (t) =$NNHC(O)R^1$ wherein $R^1$ is defined above, and
    (u) =$NNHC(O)NR^5R^6$ wherein $R^5$ and $R^6$ are defined above,
  (2) —$C_3$-alkenyl,
  (3) —$C_3$-alkynyl,
  wherein (2) and (3) can be optionally substituted with a substituent selected from the group consisting of
    (a) halogen,
    (b) carboxaldehyde,
    (c) —$CO_2R^1$ wherein $R^1$ is defined above,
    (d) —$C(O)R^1$ wherein $R^1$ is defined above,
    (e) —$C(O)NR^5R^6$ wherein $R^5$ and $R^6$ are defined above,
    (f) cyano,
    (g) aryl,
    (h) substituted aryl,
    (i) heteroaryl, and
    (j) substituted heteroaryl,
  (4) —$C_4$–$C_{10}$-alkenyl, and
  (5) —$C_4$–$C_{10}$-alkynyl,
  wherein (4) and (5) can be optionally substituted with one or more substituents independently selected from the group consisting of
    (a) halogen,
    (b) hydroxy,
    (c) —$OR^1$,
    (d) oxo,
    (e) —$NR^5R^6$ wherein $R^5$ and $R^6$ are defined above,
    (f) —$CO_2R^1$ wherein $R^1$ is defined above,
    (g) —$C(O)NR^5R^6$ wherein $R^5$ and $R^6$ are defined above,
    (h) =N—$OR^1$ wherein $R^1$ is defined above,
    (i) cyano,
    (j) $S(O)_qR^1$ wherein $R^1$ and q are defined above,
    (k) aryl,
    (l) substituted aryl,
    (m) heteroaryl,
    (n) substituted heteroaryl,
    (o) heterocycloalkyl,
    (p) substituted heterocycloalkyl,
    (q) —$NHC(O)R^1$ wherein $R^1$ is defined above,
    (r) —$NHC(O)NR^5R^6$ wherein $R^5$ and $R^6$ are defined above,
    (s) =$NNR^5R^6$ wherein $R^5$ and $R^6$ are defined above, (t) =NNHC(O)$R^1$ wherein $R^1$ is defined above, and
(u) =NNHC(O)$NR^5R^6$ wherein $R^5$ and $R^6$ are defined above;

$R^b$ is hydrogen or a hydroxy protecting group;

R is selected from the group consisting of
(1) —$C_1$–$C_{10}$-alkyl optionally substituted with one or more substituents independently selected from the group consisting of
  (a) halogen,
  (b) hydroxy,
  (c) —$OR^1$,
  (d) oxo,
  (e) —$NR^5R^6$ wherein $R^5$ and $R^6$ are defined above,
  (f) —$CO_2R^1$ wherein $R^1$ is defined above,
  (g) —C(O)$NR^5R^6$ wherein $R^5$ and $R^6$ are defined above,
  (h) =N—$OR^1$ wherein $R^1$ is defined above,
  (i) cyano,
  (j) —S(O)$_q R^1$ wherein $R^1$ and q are defined above,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)$R^1$ wherein $R^1$ is defined above,
  (r) —NHC(O)$NR^5R^6$ wherein $R^5$ and $R^6$ are defined above,
  (s) =$NNR^5R^6$ wherein $R^5$ and $R^6$ are defined above,
  (t) =NNHC(O)$R^1$ wherein $R^1$ is defined above, and
  (u) =NNHC(O)$NR^5R^6$ wherein $R^5$ and $R^6$ are defined above,
(2) —$C_3$-alkenyl,
(3) —$C_3$-alkynyl,
wherein (2) and (3) can be optionally substituted with a substituent selected from the group consisting of
  (a) halogen,
  (b) carboxaldehyde,
  (c) —$CO_2R^1$ wherein $R^1$ is defined above,
  (d) —C(O)$R^1$ wherein $R^1$ is defined above,
  (e) —C(O)$NR^5R^6$ wherein $R^5$ and $R^6$ are defined above,
  (f) cyano,
  (g) aryl,
  (h) substituted aryl,
  (i) heteroaryl,
  (j) substituted heteroaryl,
(4) —$C_4$–$C_{10}$-alkenyl, and
(5) —$C_4$–$C_{10}$-alkynyl,
wherein (4) and (5) can be optionally substituted with one or more substituents independently selected from the group consisting of
  (a) halogen,
  (b) hydroxy,
  (c) —$OR^1$ wherein $R^1$ is defined above,
  (d) oxo,
  (e) —$NR^5R^6$ wherein $R^5$ and $R^6$ are defined above,
  (f) —$CO_2R^1$ wherein $R^1$ is defined above,
  (g) —C(O)$NR^5R^6$ wherein $R^5$ and $R^6$ are defined above,
  (h) =N—$OR^1$ wherein $R^1$ is defined above,
  (i) cyano,
  (j) —S(O)$_q R^1$ wherein $R^1$ and q are defined above,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)$R^1$ wherein $R^1$ is defined above,
  (r) —NHC(O)$NR^5R^6$ wherein $R^5$ and $R^6$ are defined above,
  (s) =$NNR^5R^6$ wherein $R^5$ and $R^6$ are defined above,
  (t) =NNHC(O)$R^1$ wherein $R^1$ is defined above, and
  (u) =NNHC(O)$NR^5R^6$ wherein $R^5$ and $R^6$ are defined above;
(6) —C(O)$R^1$ wherein $R^1$ is defined above,
(7) —C(O)$OR^1$ wherein $R^1$ is defined above,
(8) —C(O)$NR^5R^6$ wherein $R^5$ and $R^6$ are defined above,
(9) hydroxyl,
(10) —$OR^1$ wherein $R^1$ is defined above,
(11) —$NR^5R^6$ wherein $R^5$ and $R^6$ are defined above, and
(12) —$SO_2R^1$ wherein $R^1$ is defined above;
and A, B, D, and E are independently selected from the group consisting of
(1) hydrogen, and
(2) —$C_1$–$C_6$-alkyl optionally substituted with one or more substituents selected from the group consisting of
  (a) —M—$R^{11}$ wherein M is selected from the group consisting of
    (i) a covalent bond,
    (ii) —C(O)NH—,
    (iii) —NHC(O)—,
    (iv) —NH—,
    (v) —N(CH$_3$)—,
    (vi) —O—,
    (vii) —S(O)$_n$— wherein n is defined above,
    (viii) —C(=NH)NH—,
    (ix) —C(O)O—,
    (x) —OC(O)—,
    (xi) —OC(O)NH—,
    (xii) —NHC(O)O—, and
    (xiii) —NHC(O)NH—,
  and
  $R^{11}$ is selected from the group consisting of
    (i) —$C_1$–$C_6$-alkyl optionally substituted with a substituent selected from the group consisting of
      (1') aryl,
      (2') substituted aryl,
      (3') heteroaryl, and
      (4') substituted heteroaryl,
    (ii) aryl,
    (iii) substituted aryl,
    (iv) heteroaryl,
    (v) substituted heteroaryl and
    (vi) heterocycloalkyl,
  (b) aryl,
  (c) substituted aryl,
  (d) heteroaryl,
  (e) substituted heteroaryl,
  (f) heterocycloalkyl,
  (g) hydroxy,
  (h) —$C_1$–$C_6$-alkoxy,
  (i) halo, and (j) —NR¹⁵R¹⁶ wherein R¹⁵ and R¹⁶, together with the nitrogen atom to which they are attached, are a 3- to 7-membered ring optionally containing therein a moiety selected from the group consisting of
(i) —O—,
(ii) —NH—,
(iii) —N(C$_1$–C$_6$-alkyl)—,
(iv) —N(C$_1$–C$_6$-alkyl substituted with aryl)—,
(v) —N(C$_1$–C$_6$-alkyl substituted with substituted aryl)—,
(vi) —N(C$_1$–C$_6$-alkyl substituted with heteroaryl)—,
(vii) —N(C$_1$–C$_6$-alkyl substituted with substituted heteroaryl)—,
(viii) —S—, and
(ix) —S(O)$_q$— wherein q is defined above, or any one pair of substituents selected from the group consisting of AB, AD, AE, BD, BE, and DE, taken together with the atom or atoms to which they are attached, are C$_3$–C$_7$-cycloalkyl or a four- to seven-membered ring containing a moiety selected from the group consisting of
(1) —O—,
(2) —NH—,
(3) —N(C$_1$–C$_6$-alkyl)—,
(4) —N(C$_1$–C$_6$-alkyl substituted with aryl)—,
(5) —N(C$_1$–C$_6$-alkyl substituted with substituted aryl)—,
(6) —N(C$_1$–C$_6$-alkyl substituted with heteroaryl)—,
(7) —N(C$_1$–C$_6$-alkyl substituted with substituted heteroaryl)—, and
(8) —S(O)$_q$— wherein q is defined above.

In another embodiment of the invention are pharmaceutical compositions comprising a therapeutically effective amount of a compound of formulas (I)–(III) with a pharmaceutically acceptable carrier.

In another embodiment of the invention are methods of treating bacterial infection in a mammal in recognized need of such treatment comprising administering an effective amount of a compound of formulas (I)–(III).

In another embodiment of the invention is disclosed a process for the preparation of a compound of formula (I)

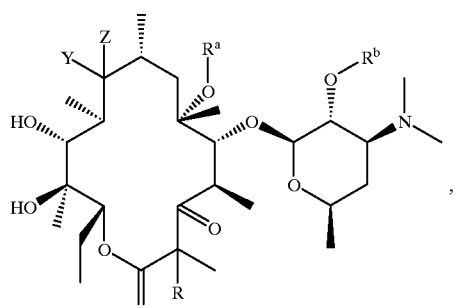

(I)

a compound of formula (II)

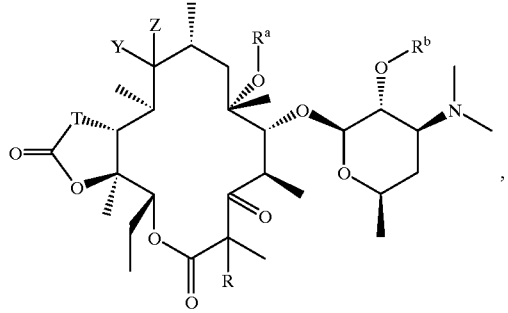

(II)

and a compound of formula (III)

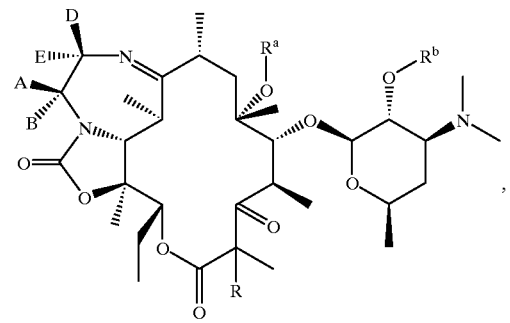

(III)

wherein, in formulas (I)–(III),

Y and Z together are selected from the group consisting of
(1) oxo,
(2) =N—OH,
(3) =N—OR¹ wherein R¹ is selected from the group consisting of
(a) —C$_1$–C$_{12}$-alkyl,
(b) —C$_1$–C$_{12}$-alkyl substituted with aryl,
(c) —C$_1$–C$_{12}$-alkyl substituted with substituted aryl,
(d) —C$_1$–C$_{12}$-alkyl substituted with heteroaryl,
(e) —C$_1$–C$_{12}$-alkyl substituted with substituted heteroaryl,
(f) —C$_3$–C$_{12}$-cycloalkyl,
(g) —Si(R²)(R³)(R⁴), wherein R², R³, and R⁴, are each independently —C$_1$–C$_{12}$-alkyl or aryl, and
(h) —(CH$_2$)$_n$NR⁵R⁶ wherein n is two to six, and R⁵ and R⁶ are independently selected from the group consisting of
(i) hydrogen,
(ii) —C$_1$–C$_{12}$-alkyl,
(iii) —C$_1$–C$_{12}$-alkyl substituted with aryl,
(iv) —C$_1$–C$_{12}$-alkyl substituted with substituted aryl,
(v) —C$_1$–C$_{12}$-alkyl substituted with heteroaryl, and
(vi) —C$_1$–C$_{12}$-alkyl substituted with substituted heteroaryl, or R$^5$ and R$^6$ taken together with the atom to which they are attached are C$_3$–C$_{12}$-heterocycloalkyl, and (4) =N—OC(R$^7$)(R$^8$)(—OR$^1$), wherein R$^1$ is defined above, and R$^7$ and R$^8$ are independently selected from the group consisting of
  (i) hydrogen,
  (ii) —C$_1$–C$_{12}$-alkyl,
  (iii) —C$_1$–C$_{12}$-alkyl substituted with aryl,
  (iv) —C$_1$–C$_{12}$-alkyl substituted with substituted aryl,
  (v) —C$_1$–C$_{12}$-alkyl substituted with heteroaryl, and
  (vi) —C$_1$–C$_{12}$-alkyl substituted with substituted heteroaryl,
or R$^7$ and R$^8$ taken together with the atom to which they are attached are C$_3$–C$_{12}$-cycloalkyl, or one of Y and Z is hydrogen, and the other is selected from the group consisting of
(1) hydrogen,
(2) hydroxy,
(3) —OR$^1$ wherein R$^1$ is defined above, and
(4) —NR$^5$R$^6$ wherein R$^5$ and R$^6$ are defined above;

T is selected from the group consisting of
(1) —O—,
(2) —NH—, and
(3) —N(W(R$^g$))— wherein W is absent or selected from the group consisting of
  (a) —O—,
  (b) —(CH$_2$)$_p$— wherein p is one to six, and
  (c) —NH—,
and
R$^g$ is selected from the group consisting of
  (a) hydrogen,
  (b) —C$_3$–C$_7$-cycloalkyl,
  (c) aryl,
  (d) substituted aryl,
  (e) heteroaryl,
  (f) substituted heteroaryl,
  (g) —C$_1$–C$_6$-alkyl,
  (h) —NR$^5$R$^6$ wherein R$^5$ and R$^6$ are defined above, and
  (i) —C$_1$–C$_6$-alkyl substituted with one or more substituents independently selected from the group consisting of
    (i) aryl,
    (ii) substituted aryl,
    (iii) heteroaryl,
    (iv) substituted heteroaryl,
    (v) hydroxy,
    (vi) —OR$^1$, and
    (vii) —NR$^5$R$^6$ wherein R$^5$ and R$^6$ are defined above;

R$^a$ is selected from the group consisting of
(1) —C$_1$–C$_{10}$-alkyl optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein RI is defined above,
  (i) cyano,
  (j) —S(O)$_q$R$^1$ wherein R$^1$ is defined above and q is zero to two,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and
  (u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
  (a) halogen,
  (b) carboxaldehyde,
  (c) —CO$_2$R$^1$ wherein R$^1$ is defined above,
  (d) —C(O)R$^1$ wherein R$^1$ is defined above,
  (e) —C(O)NR$^5$R$^6$ wherein R$^5$ and R$^6$ are defined above,
  (f) cyano,
  (g) aryl,
  (h) substituted aryl,
  (i) heteroaryl, and
  (j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein R$^1$ is defined above,
  (i) cyano,
  (j) —S(O)$_q$R$^1$ wherein R$^1$ and q are defined above,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and
  (u) =NNHC(O)NR$^5$R$^6$ wherein R$^5$ and R$^6$ are defined above;

R$^b$ is hydrogen or a hydroxy protecting group;

R is selected from the group consisting of
(1) —C$_1$–C$_{10}$-alkyl optionally substituted with one or more substituents independently selected from the group consisting of
  (a) halogen,
  (b) hydroxy, (c) —OR$^1$,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
(a) halogen,
(b) carboxaldehyde,
(c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
(a) halogen,
(b) hydroxy,
(c) —OR$^1$ wherein R$^1$ is defined above,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;

(4) —C(O)R$^1$ wherein R$^1$ is defined above,
(5) —C(O)OR$^1$ wherein R$^1$ is defined above,
(6) —C(O)NR$^5$R$^6$ wherein R$^5$ and R$^6$ are defined above,
(7) hydroxyl,
(8) —OR$^1$ wherein R$^1$ is defined above,
(9) —NR$^5$R$^6$ wherein R$^5$ and R$^6$ are defined above, and
(10) —SO$_2$R$^1$ wherein R$^1$ is defined above;
and
A, B, D, and E are independently selected from the group consisting of
(1) hydrogen, and
(2) —C$_1$–C$_6$-alkyl optionally substituted with one or more substituents selected from the group consisting of
(a) —M—R$^{11}$ wherein M is selected from the group consisting of
(i) a covalent bond,
(ii) —C(O)NH—,
(iii) —NHC(O)—,
(iv) —NH—,
(v) —N(CH$_3$)—,
(vi) —O—,
(vii) —S(O)$_n$— wherein n is defined above,
(viii) —C(=NH)NH—,
(ix) —C(O)O—,
(x) —OC(O)—,
(xi) —OC(O)NH—,
(xii) —NHC(O)O—, and
(xiii) —NHC(O)NH—,
and
R$^{11}$ is selected from the group consisting of
(i) —C$_1$–C$_6$-alkyl optionally substituted with a substituent selected from the group consisting of
(1') aryl,
(2') substituted aryl,
(3') heteroaryl, and
(4') substituted heteroaryl,
(ii) aryl,
(iii) substituted aryl,
(iv) heteroaryl,
(v) substituted heteroaryl and
(vi) heterocycloalkyl,
(b) aryl,
(c) substituted aryl,
(d) heteroaryl,
(e) substituted heteroaryl,
(f) heterocycloalkyl,
(g) hydroxy,
(h) —C$_1$–C$_6$-alkoxy,
(i) halo, and
(j) —NR$^{15}$R$^{16}$ wherein R$^{15}$ and R$^{16}$, together with the nitrogen atom to which they are attached, are a 3- to 7-membered ring optionally containing therein a moiety selected from the group consisting of
(i) —O—,
(ii) —NH—,
(iii) —N(C$_1$–C$_6$-alkyl)—, (iv) —N($C_1$–$C_6$-alkyl-substituted with aryl)—,
(v) —N($C_1$–$C_6$-alkyl substituted with substituted aryl)—,
(vi) —N($C_1$–$C_6$-alkyl substituted with heteroaryl)—,
(vii) —N($C_1$–$C_6$-alkyl substituted with substituted heteroaryl)—,
(viii) —S—, and
(ix) —S(O)$_q$— wherein q is defined above, or any one pair of substituents selected from the group consisting of AB, AD, AE, BD, BE, and DE, taken together with the atom or atoms to which they are attached, are $C_3$–$C_7$-cycloalkyl or a four- to seven-membered ring containing a moiety selected from the group consisting of (1) —O—,
(2) —NH—,
(3) —N($C_1$–$C_6$-alkyl)—,
(4) —N($C_1$–$C_6$-alkyl substituted with aryl)—,
(5) —N($C_1$–$C_6$-alkyl substituted with substituted aryl)—,
(6) —N($C_1$–$C_6$-alkyl substituted with heteroaryl)—,
(7) —N($C_1$–$C_6$-alkyl substituted with substituted heteroaryl)—, and
(8) —S(O)$_q$— wherein q is defined above, the process comprising (a) reacting a compound of formula (Ia)

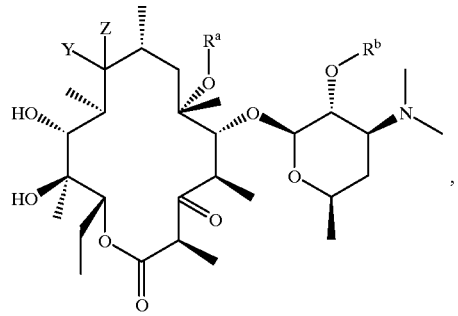

a compound of formula (IIa)

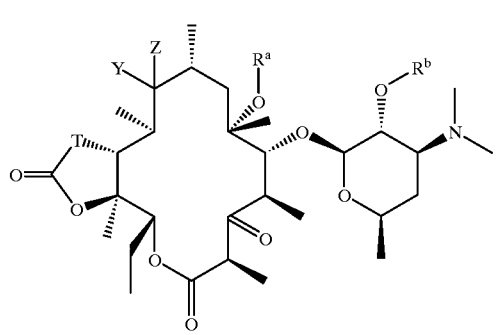

or a compound of formula (IIIa)

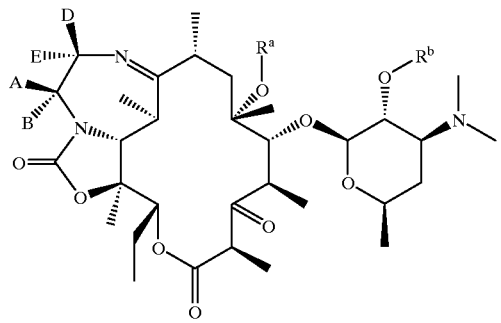

with an electrophile in the presence of a base, and (b) optionally deprotecting and isolating the desired product.

In another embodiment of the invention is a process for the preparation of a compound of formula (I)

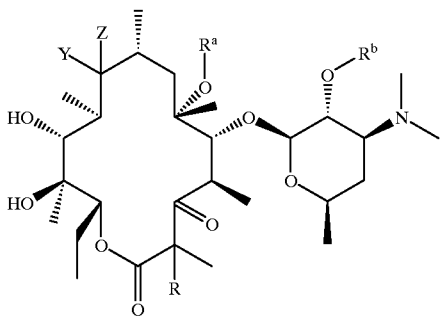

a compound of formula (II)

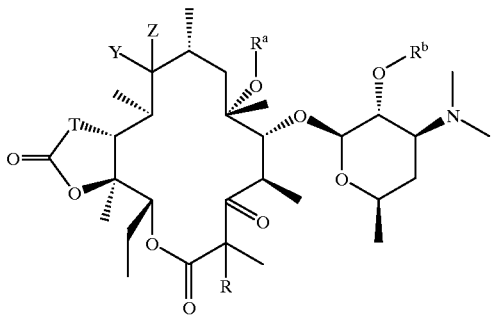

and
a compound of formula (III)

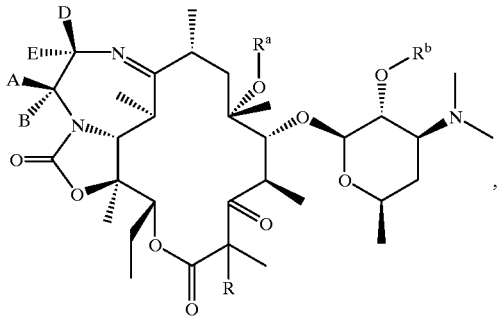

(III)

wherein, in formulas (I)–(III),
Y and Z together are selected from the group consisting of
(1) oxo,
(2) =N—OH,
(3) =N—OR$^1$ wherein R$^1$ is selected from the group consisting of
  (a) —C$_1$–C$_{12}$-alkyl,
  (b) —C$_1$–C$_{12}$-alkyl substituted with aryl,
  (c) —C$_1$–C$_{12}$-alkyl substituted with substituted aryl,
  (d) —C$_1$–C$_{12}$-alkyl substituted with heteroaryl,
  (e) —C$_1$–C$_{12}$-alkyl substituted with substituted heteroaryl,
  (f) —C$_3$–C$_{12}$-cycloalkyl,
  (g) —Si(R$^2$)(R$^3$)(R$^4$), wherein R$^2$, R$^3$, and R$^4$, are each independently —C$_1$–C$_{12}$- alkyl or aryl, and
  (h) —(CH$_2$)$_n$NR$^5$R$^6$ wherein n is two to six, and R$^5$ and R$^6$ are independently selected from the group consisting of
    (i) hydrogen,
    (ii) —C$_1$–C$_{12}$-alkyl,
    (iii) —C$_1$–C$_{12}$-alkyl substituted with aryl,
    (iv) —C$_1$–C$_{12}$-alkyl substituted with substituted aryl,
    (v) —C$_1$–C$_{12}$-alkyl substituted with heteroaryl, and
    (vi) —C$_1$–C$_{12}$-alkyl substituted with substituted heteroaryl,
    or
    R$^5$ and R$^6$ taken together with the atom to which they are attached are C$_3$–C$_{12}$-cycloalkyl,
  and
(4) =N—OC(R$^7$)(R$^8$)(—OR$^1$), wherein R$^1$ is defined above, and R$^7$ and R$^8$ are independently selected from the group consisting of
  (i) hydrogen,
  (ii) —C$_1$–C$_{12}$-alkyl,
  (iii) —C$_1$–C$_{12}$-alkyl substituted with aryl,
  (iv) —C$_1$–C$_{12}$-alkyl substituted with substituted aryl,
  (v) —C$_1$–C$_{12}$-alkyl substituted with heteroaryl, and
  (vi) —C$_1$–C$_{12}$-alkyl substituted with substituted heteroaryl,
  or
  R$^7$ and R$^8$ taken together with the atom to which they are attached are C$_3$–C$_{12}$-cycloalkyl,
or
one of Y and Z is hydrogen, and the other is selected from the group consisting of
(1) hydrogen,
(2) hydroxy,
(3) —OR$^1$ wherein R$^1$ is defined above, and
(4) —NR$^5$R$^6$ wherein R$^5$ and R$^6$ are defined above;
T is selected from the group consisting of
(1) —O—,
(2) —NH—, and
(3) —N(W(R$^g$))— wherein W is absent or selected from the group consisting of
  (a) —O—,
  (b) —(CH$_2$)$_p$— wherein p is one to six, and
  (c) —NH—,
  and
  R$^g$ is selected from the group consisting of
  (a) hydrogen,
  (b) —C$_3$–C$_7$-cycloalkyl,
  (c) aryl,
  (d) substituted aryl,
  (e) heteroaryl,
  (f) substituted heteroaryl,
  (g) —C$_1$–C$_6$-alkyl,
  (h) —NR$^5$R$^6$ wherein R$^5$ and R$^6$ are defined above, and
  (i) —C$_1$–C$_6$-alkyl substituted with one or more substituents independently selected from the group consisting of
    (i) aryl,
    (ii) substituted aryl,
    (iii) heteroaryl,
    (iv) substituted heteroaryl,
    (v) hydroxy,
    (vi) —OR$^1$, and
    (vii) —NR$^5$R$^6$ wherein R$^5$ and R$^6$ are defined above;
R$^a$ is selected from the group consisting of
(1) —C$_1$–C$_{10}$-alkyl optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein R$^1$ is defined above,
  (i) cyano,
  (j) —S(O)$_q$R$^1$ wherein R$^1$ is defined above and q is zero to two,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and
  (u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
  (a) halogen,
  (b) carboxaldehyde, (c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
(a) halogen,
(b) hydroxy,
(c) —OR,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;

R$^b$ is hydrogen or a hydroxy protecting group;
R is selected from the group consisting of
(1) —C$_1$–C$_{10}$-alkyl optionally substituted with one or more substituents independently selected from the group consisting of
(a) halogen,
(b) hydroxy,
(c) —ORI,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above, (2) —C$_3$-alkenyl,
(3) —C$_3$-alkynyl,
wherein (2) and (3) can be optionally substituted with a substituent selected from the group consisting of
(a) halogen,
(b) carboxaldehyde,
(c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
(a) halogen,
(b) hydroxy,
(c) —OR$^1$ wherein R$^1$ is defined above,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—ORI wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;
(4) —C(O)R$^1$ wherein R$^1$ is defined above,
(5) —C(O)OR$^1$ wherein R$^1$ is defined above,
(6) —C(O)NR$^5$R$^6$ wherein R$^5$ and R$^6$ are defined above,
(7) hydroxyl,
(8) —OR$^1$ wherein R$^1$ is defined above,
(9) —NR$^5$R$^6$ wherein R$^5$ and R$^6$ are defined above, and
(10) —SO$_2$R$^1$ wherein R$^1$ is defined above;
and
A, B, D, and E are independently selected from the group consisting of
(1) hydrogen, and
(2) —C$_1$–C$_6$-alkyl optionally substituted with one or more substituents selected from the group consisting of
(a) —M—R$^{11}$ wherein M is selected from the group consisting of
(i) a covalent bond,
(ii) —C(O)NH—,
(iii) —NHC(O)—,
(iv) —NH—,
(v) —N(CH$_3$)—,
(vi) —O—, (vii) —S(O)$_n$— wherein n is defined above,
(viii) —C(=NH)NH—,
(ix) —C(O)O—,
(x) —OC(O)—,
(xi) —OC(O)NH—,
(xii) —NHC(O)O—, and
(xiii) —NHC(O)NH—,
and
R$^{11}$ is selected from the group consisting of
(i) —C$_1$–C$_6$-alkyl optionally substituted with a substituent selected from the group consisting of
(1') aryl,
(2') substituted aryl,
(3') heteroaryl, and
(4') substituted heteroaryl,
(ii) aryl,
(iii) substituted aryl,
(iv) heteroaryl,
(v) substituted heteroaryl and
(vi) heterocycloalkyl,
(b) aryl,
(c) substituted aryl,
(d) heteroaryl,
(e) substituted heteroaryl,
(f) heterocycloalkyl,
(g) hydroxy,
(h) —C$_1$–C$_6$-alkoxy,
(i) halo, and
(j) —NR$^{15}$R$^{16}$ wherein R$^{15}$ and R$^{16}$, together with the nitrogen atom to which they are attached, are a 3- to 7-membered ring optionally containing therein a moiety selected from the group consisting of
(i) —O—,
(ii) —NH—,
(iii) —N(C$_1$–C$_6$-alkyl)—,
(iv) —N(C$_1$–C$_6$-alkyl-substituted with aryl)—,
(v) —N(C$_1$–C$_6$-alkyl substituted with substituted aryl)—,
(vi) —N(C$_1$–C$_6$-alkyl substituted with heteroaryl)—,
(vii) —N(C$_1$–C$_6$-alkyl substituted with substituted heteroaryl)—,
(viii) —S—, and
(ix) —S(O)$_q$— wherein q is defined above,
or
any one pair of substituents selected from the group consisting of AB, AD, AE, BD, BE, and DE, taken together with the atom or atoms to which they are attached, are C$_3$–C$_7$-cycloalkyl or a four- to seven-membered ring containing a moiety selected from the group consisting of
(1) —O—,
(2) —NH—,
(3) —N(C$_1$–C$_6$-alkyl)—,
(4) —N(C$_1$–C$_6$-alkyl substituted with aryl)—,
(5) —N(C$_1$–C$_6$-alkyl substituted with substituted aryl)—,
(6) —N(C$_1$–C$_6$-alkyl substituted with heteroaryl)—,
(7) —N(C$_1$–C$_6$-alkyl substituted with substituted heteroaryl)—, and
(8) —S(O)$_q$— wherein q is defined above, the process comprising
(a) reacting the compound of formula (Ia)

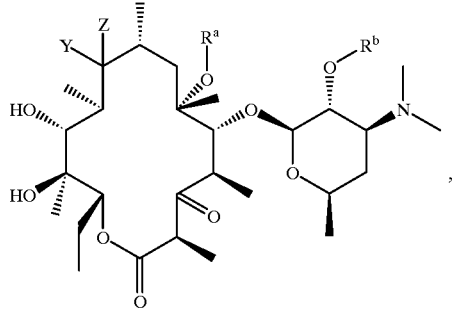

(Ia)

a compound of formula (IIa)

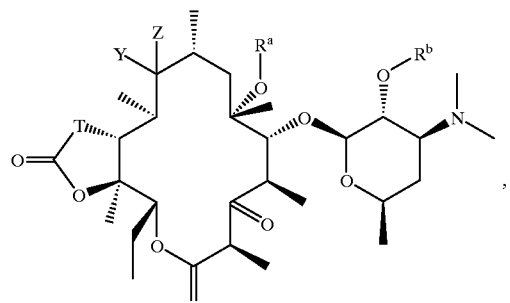

(IIa)

or
a compound of formula (IIIa)

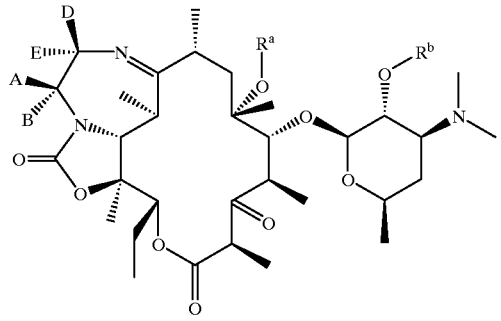

(IIIa)

with an oxidizing agent
and
(b) optionally deprotecting and isolating the desired product.

DETAILED DESCRIPTION OF THE INVENTION

Definition of Terms

The term "alkenyl," as used herein, refers to a monovalent straight or branched chain group containing at least one carbon-carbon double bond. The alkenyl groups of this invention can be optionally substituted.

The term alkyl," as used herein, refers to saturated, straight or branched chain hydrocarbon radicals. Examples of alkyl radicals include methyl, ethyl, propyl, iso-propyl, n-butyl, tert-butyl, neo-pentyl, and n-hexyl. The alkyl groups of this invention can be optionally substituted.

The term "—$C_1$–$C_3$-alkylamino," as used herein, refers to a amino group, as defined herein wherein one hydrogen atom is replaced by a —$C_1$–$C_3$-alkyl group. Examples of —$C_1$–$C_3$-alkylamino include methylamine, ethylamine, propylamine, and iso-propylamine.

The term "—$C_1$–$C_3$-alkylthio," as used herein, refers to a —$C_1$–$C_3$-alkyl group, as defined herein, attached to the parent molecular group through a sulfur atom. Examples of —$C_1$–$C_3$-alkylthio include methyl sulfide, ethyl sulfide, propyl sulfide, and iso-propyl sulfide.

The term "alkoxy," as used herein, refers to an alkyl group, as previously defined, attached to the parent molecular group through an oxygen atom. Examples of alkoxy include methoxy, ethoxy, propoxy, isopropoxy, n-butoxy, tert-butoxy, neo-pentoxy and n-hexoxy. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "amino," as used herein, refers to —$NH_2$.

The term "aprotic solvent," as used herein, refers to a solvent that is relatively inert to proton activity, i e., not acting as a proton donor. Examples include hydrocarbons such as hexane and toluene, halogenated hydrocarbons such as dichloromethane, ethylene chloride, and chloroform, heterocyclic compounds such as tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick, et al., Vol. 11, in the Techniques of Chemistry Series, John Wiley & Sons, NY, 1986.

The term "aryl" as used herein refers to unsubstituted carbocyclic aromatic groups including phenyl, naphthyl, and anthracenyl.

The term "arylamino," as used herein, refers to a amino group, as defined herein wherein one hydrogen atom is replaced by an aryl group, as defined herein.

The term "aryloxy," as used herein, refers to an aryl group, as defined herein, attached to the parent molecular group through an oxygen atom.

The term "arylthio," as used herein, refers to an aryl group, as defined herein, attached to the parent molecular group through a sulfur atom.

The term "azido," as used herein, refers to —$N_3$.

The term "benzyl," as used herein, refers to —$CH_2C_6H_5$.

The term "benzyloxy," as used herein, refers to a benzyl group, as defined herein, attached to the parent molecular group through an oxygen atom.

The term "benzylamino," as used herein, refers to a amino group, as defined herein wherein one hydrogen atom is replaced by a benzyl group, as defined herein.

The term "benzylthio," as used herein, refers to an benzyl group, as defined herein, attached to the parent molecular group through a sulfur atom.

The term "carboxaldehyde," as used herein, refers to —CHO.

The term "cyano," as used herein, refers to —CN.

The term "cycloalkyl," as used herein, refers to saturated carbocyclic groups having three to seven carbons such as cyclopropyl, cyclobutyl, cyclopentyl, cyclohexyl, and cycloheptyl.

The term "halo," as used herein, refers to —F, —Cl, —Br, and —I.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. The nitrogen atoms can optionally be quatemized, and the sulfur atoms can optionally be oxidized. Heteroaryl groups of this invention include those derived from furan, imidazole, isothiazole, isoxazole, oxadiazole, oxazole, 1,2,3-oxadiazole, pyrazine, pyrazole, pyridazine, pyridine, pyrimidine, pyrroline, quinoline, thiazole, 1,3,4-thiadiazole, thiene, triazole, and tetrazole.

The term "heteroarylamino," as used herein, refers to a amino group, as defined herein wherein one hydrogen atom is replaced by a heteroaryl group, as defined herein.

The term "heteroaryloxy," as used herein, refers to a heteroaryl group, as defined herein, attached to the parent molecular group through an oxygen atom.

The term "heteroarylthio," as used herein, refers to a heteroaryl group, as defined herein, attached to the parent molecular group through a sulfur atom.

The term "heterocycloalkyl" as used herein, refers to a non-aromatic five-, six- or seven-membered ring or a bi- or tri-cyclic group comprising fused six-membered rings having between one and three heteroatoms independently selected from oxygen, sulfur and nitrogen wherein each 5-membered ring has zero to one double bonds and each six-membered ring has zero to 2 double bonds, the nitrogen and sulfur heteroatoms may optionally be oxidized, the nitrogen heteroatom may optionally be quatemized, and any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy," as used herein, refers to —OH.

The term "hydroxy protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis,* 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "methoxymethoxy," as used herein, refers to —$OCH_2OCH_3$.

The term "methoxyethoxy," as used herein, refers to —$OCH_2OCH_2CH_3$.

The term "methylthiomethyl," as used herein, refers to —$CH_2SCH_3$.

The term "oxo," as used herein, refers to a group formed by the replacement of two hydrogen atoms on the same carbon atom of an alkyl group, as defined above, with a single oxygen atom and is exemplified by a carbonyl group.

A the term "protected hydroxy" refers to a hydroxy group protected with a hydroxy protecting group, as defined above, such as benzoyl, acetyl, trimethylsilyl, triethylsilyl, methoxymethyl groups, for example.

The term "protogenic organic solvent," as used herein, refers to a solvent that provides protons such as methanol, ethanol, propanol, iso propanol, butanol, and tert-butanol. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick, et al., Vol. 11, in the Techniques of Chemistry Series, John Wiley & Sons, NY, 1986.

The term "substituted aryl," as used herein, refers to an aryl group, as defined herein, substituted by independent replacement of one, two or three of the hydrogen atoms thereon with —F, —Cl, —Br, —I, —OH, —NO$_2$, —CN, —C(O)-C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH-C$_1$–C$_6$-alkyl, —CONH-aryl, —CONH-heteroaryl, —OC(O)-C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH-C$_1$–C$_6$-alkyl, —OCONH-aryl, —OCONH-heteroaryl, —NHC(O)-C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH-C$_1$–C$_6$-alkyl, —NHCONH-aryl, —NHCONH-heteroaryl, —SO$_2$-C$_1$–C$_6$-alkyl, —SO$_2$-aryl, —SO$_2$-heteroaryl, —SO$_2$NH$_2$, —SO$_2$NH-C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxy, methoxymethoxy, methoxyethoxy, amino, benzylamino, arylamino, heteroarylamino, —C$_1$–C$_3$-alkylamino, thio, arylthio, heteroarylthio, benzylthio, —C$_1$–C$_6$-alkylthio, or methylthiomethyl.

The term "substituted heteroaryl" as used herein refers to a heteroaryl group as defined herein substituted by independent replacement of one, two or three of the hydrogen atoms thereon with —F, —Cl, —Br, —I, —OH, —NO$_2$, —CN, —C(O)-C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH-C$_1$–C$_6$-alkyl, —CONH-aryl, —CONH-heteroaryl, —OC(O)-C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH-C$_1$–C$_6$-alkyl, —OCONH-aryl, —OCONH-heteroaryl, —NHC(O)-C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH-C$_1$–C$_6$-alkyl, —NHCONH-aryl, —NHCONH-heteroaryl, —SO$_2$-C$_1$–C$_6$-alkyl, —SO$_2$-aryl, —SO$_2$-heteroaryl, —SO$_2$NH$_2$, —SO$_2$NH-C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxy, methoxymethoxy, methoxyethoxy, amino, benzylamino, arylamino, heteroarylamino, —C$_1$–C$_3$-alkylamino, thio, arylthio, heteroarylthio, benzylthio, —C$_1$–C$_6$-alkylthio, or methylthiomethyl.

The term "substituted heterocycloalkyl," as used herein, refers to a heterocycloalkyl group, as defined above, substituted by independent replacement of one, two or three of the hydrogen atoms thereon with —F, —Cl, —Br, —I, —OH, —NO$_2$, —CN, —C(O)-C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH-C$_1$–C$_6$-alkyl, —CONH-aryl, —CONH-heteroaryl, —OC(O)-C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH-C$_1$–C$_6$-alkyl, —OCONH-aryl, —OCONH-heteroaryl, —NHC(O)-C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH-C$_1$–C$_6$-alkyl, —NHCONH-aryl, —NHCONH-heteroaryl, —SO$_2$-C$_1$–C$_6$-alkyl, —SO$_2$-aryl, —SO$_2$-heteroaryl, —SO$_2$NH$_2$, —SO$_2$NH-C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, —C$_1$–C$_3$-alkylamino, thio, arylthio, heteroarylthio, benzylthio, alkylthio, or methylthiomethyl.

The term "thio," as used herein, refers to —SH.

Numerous asymmetric centers may exist in the compounds of the present invention. Except where otherwise noted, the present invention contemplates the various stereoisomers and mixtures thereof. Accordingly, whenever a bond is represented by a wavy line or a straight line, it is intended that a mixture of stereo-orientations or an individual isomer of unassigned orientation may be present.

The term "pharmaceutically acceptable salt," as used herein, refers to those salts which are, within the scope of sound medical judgment, suitable for use in contact with the tissues of humans and lower animals without undue toxicity, irritation, and allergic response and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention or separately by reacting a free base group with a suitable organic acid. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically acceptable ester," as used herein, refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters includes formates, acetates, propionates, butyates, acrylates, and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Preferred compounds of the invention include

Compound of formula (II): $R^a$ is $CH_3$, $R^b$ is H, Y and Z together are O, T is —NH—, R is —$CH_2CH=CH$-(phenyl), Compound of formula (II): $R^a$ is $CH_3$, $R^b$ is H, Y and Z together are O, T is —N(W($R^g$))—, W is —$(CH_2)_p$—, p is 4, $R^g$ is phenyl, R is —OH, Compound of formula (II): $R^a$ is —$CH_2CH=CH$-(3-quinolinyl), $R^b$ is H, Y and Z together are O, T is —NH—, R is —$CH_2CH=CH_2$, Compound of formula (II): $R^a$ is —$CH_2CH=CH$-(3-quinolinyl), $R^b$ is H, Y and Z together are O, T is —NH—, R is —$CH_2CO_2C_2H_5$, Compound of formula (III): $R^a$ is $CH_3$, $R^b$ is H, Y and Z together are O, A is —$CH_2OH$, B,D, and E are H, R is —$CH_2$-(4-chlorophenyl), Compound of formula (I): $R^a$ is $CH_3$, $R^b$ is —$C(O)C_6H_5$, Y and Z together are O, R is —OH, Compound of formula (II): $R^a$ is —$CH_2CH=CH$-(3-quinolinyl), $R^b$ is H, Y and Z together are O, T is —NH—, R is —OH, Compound of formula (II): $R^a$ is —$CH_2C\equiv CH$, $R^b$ is H, Y and Z together are O, T is —NH—, R is —$CH_2CH=CH$-(phenyl), Compound of formula (II): $R^a$ is $CH_3$, $R^b$ is H, Y and Z together are O, T is —N(W($R^g$))—, W is —$(CH_2)_p$—, p is 4, $R^g$ is phenyl, R is —$SO_2CH_3$, Compound of formula (II): $R^a$ is $CH_3$, $R^b$ is H, Y and Z together are O, T is —N(W($R^g$))—, W is —$(CH_2)_p$—, p is 2, $R^g$ is amino, R is —$SO_2CH_3$, Compound of formula (II): $R^a$ is $CH_3$, $R^b$ is H, Y and Z together are O, T is —NH—, R is —$CH_2CH=CH_2$, Compound of formula (II): $R^a$ is $CH_3$, $R^b$ is H, Y and Z together are O, T is —NH—, R is —$CH_2CH_3$, Compound of formula (II): $R^a$ is $CH_3$, $R^b$ is H, Y and Z together are O, T is —NH—, R is —$CH_2CO_2CH_3$, Compound of formula (II): $R^a$ is $CH_3$, $R^b$ is H, Y and Z together are O, T is —NH—, R is —$CH_2CH_2CO_2CH_3$, Compound of formula (II): $R^a$ is $CH_3$, $R^b$ is H, Y and Z together are O, T is —NH—, R is —$CH_2C(O)$(phenyl), Compound of formula (II): $R^a$ is $CH_3$, $R^b$ is H, Y and Z together are O, T is —NH—, R is benzyl, Compound of formula (II): $R^a$ is $CH_3$, $R^b$ is H, Y and Z together are O, T is —NH—, R is —$CH_2$-(4-tert-butylphenyl), Compound of formula (II): $R^a$ is $CH_3$, $R^b$ is H, Y and Z together are O, T is —NH—, R is —1,1'-biphenyl-2-ylmethyl, Compound of formula (II): $R^a$ is $CH_3$, $R^b$ is H, Y and Z together are O, T is —NH—, R is —$CH_2$-(3-chlorophenyl), Compound of formula (II): $R^a$ is $CH_3$, $R^b$ is H, Y and Z together are O, T is —NH—, R is —$CH_2CH_2CH$=CH-(phenyl), Compound of formula (II): $R^a$ is $CH_3$, $R^b$ is H, Y and Z together are O, T is —NH—, R is —$CH_2$-(3-naphthyl), Compound of formula (II): $R^a$ is $CH_3$, $R^b$ is H, Y and Z together are O, T is —NH—, R is —$CH_2$-(9-anthracenyl), and Compound of formula (II): $R^a$ is $CH_3$, $R^b$ is H, Y and Z together are O, T is —NH—, R is —$CH_2$-(4-fluorophenyl).

Determination of Biological Activity

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1, demonstrate the antibacterial activity of the compounds of the invention.

| Microorganism | Code |
|---|---|
| *Staphylococcus aureus* ATCC 6538P | AA |
| *Staphylococcus aureus* A-5177 | BB |
| *Staphylococcus aureus* A-5278 | CC |
| *Staphylococcus aureus* CMX 642A | DD |
| *Staphylococcus aureus* NCTC 10649M | EE |
| *Staphylococcus aureus* CMX 553 | FF |
| *Staphylococcus aureus* 1775 | GG |
| *Staphylococcus epidermidis* 3519 | HH |
| Enterococcusfaecium ATCC X043 | II |
| *Streptococcus bovis* A-5169 | JJ |
| *Streptococcus agalactiae* CMX 508 | KK |
| *Streptococcus pyogenes* EES61 | LL |
| *Streptococcus pyogenes* 930 | MM |
| *Streptococcus pyogenes* PIU 2548 | NN |
| Micrococcusluteus ATCC 9341 | OO |
| Micrococcusluteus ATCC 4698 | PP |
| Escherichiacoli JUHL | QQ |
| Escherichiacoli SS | RR |
| Escherichiacoli DC-2 | SS |
| *Candida albicans* CCH 442 | TT |
| *Mycobacterium smegmatis* ATCC 114 | UU |
| Nocardia Asteroides ATCC 99700 | VV |
| HaemophilisInfluenzae DILL AMP R | WW |
| Streptococcus Pneumonia ATCC 6303 | XX |
| Streptococcus Pneumonia GYR 1171 | YY |
| Streptococcus Pneumonia 5979 | ZZ |
| Streptococcus Pneumonia 5649 | ZA |

TABLE 1

Antibacterial Activity (MIC's) of Selected Compounds

| | Ery. A standard | Example 1 | Example 2 | Example 3 | Example 4 | Example 8 | Example 9 | Example 10 |
|---|---|---|---|---|---|---|---|---|
| AA | 0.2 | 25 | 1.56 | >100 | 0.78 | 0.39 | 3.1 | 1.56 |
| BB | 3.1 | 25 | 1.56 | >100 | 0.39 | 0.39 | 3.1 | 1.56 |
| CC | >100 | 100 | 100 | >100 | >100 | >100 | >100 | 25 |
| DD | 0.39 | 25 | 3.1 | >100 | 0.78 | 0.39 | 3.1 | 1.56 |
| EE | 0.39 | 50 | 1.56 | >100 | 0.78 | 0.78 | 12.5 | 1.56 |
| FF | 0.39 | 50 | 1.56 | >100 | 0.39 | 0.78 | 3.1 | 1.56 |
| GG | >100 | 100 | 100 | >100 | >100 | >100 | >100 | 25 |
| HH | 0.39 | 50 | 3.1 | >100 | 0.39 | 0.39 | 6.2 | 1.56 |
| II | 0.05 | 25 | 0.39 | 100 | 0.2 | 0.2 | 3.1 | 0.39 |
| JJ | 0.02 | 12.5 | 0.2 | 50 | 0.05 | 0.02 | 0.78 | 0.2 |
| KK | 0.05 | 12.5 | 0.2 | 50 | 0.2 | 0.01 | 1.56 | 0.2 |
| LL | 0.05 | 12.5 | 0.1 | 100 | 0.1 | 0.02 | 1.56 | 0.2 |

TABLE 1-continued

Antibacterial Activity (MIC's) of Selected Compounds

|     | Ery. A standard | Example 1 | Example 2 | Example 3 | Example 4 | Example 8 | Example 9 | Example 10 |
|-----|---|---|---|---|---|---|---|---|
| MM  | >100 | 50 | 25 | >100 | 12.5 | 50 | 50 | 6.2 |
| NN  | 6.2 | 12.5 | 0.39 | >100 | 0.78 | 0.39 | 3.1 | 1.56 |
| OO  | 0.05 | 3.1 | 0.39 | 50 | 0.1 | 0.02 | 1.56 | 0.39 |
| PP  | 0.2 | 6.2 | 0.78 | >100 | 0.78 | 0.2 | 3.1 | 0.39 |
| QQ  | >100 | >100 | >100 | >100 | >100 | >100 | >100 | >100 |
| RR  | 0.78 | 50 | 6.2 | 100 | 3.1 | 0.2 | 6.2 | 3.1 |
| SS  | >100 | >100 | >100 | >100 | >100 | >100 | >100 | >100 |
| TT  | >100 | 100 | 100 | >100 | >100 | >100 | >100 | 25 |
| UU  | 3.1 | 25 | 3.1 | >100 | 3.1 | 3.1 | 12.5 | 1.56 |
| VV  | 0.1 | 25 | 3.1 | >100 | 0.1 | 0.39 | 1.56 | 1.56 |
| WW  | 4 | >128 | 64 | >128 | 16 | 16 | >64 | 16 |
| XX  | 0.06 | 8 | 0.5 | 64 | 0.25 | 0.03 | 1 | — |
| YY  | 0.06 | 4 | 0.25 | 32 | 0.25 | 0.03 | 1 | — |
| ZZ  | >128 | 64 | 32 | >128 | 64 | 128 | 64 | — |
| ZZA | 16 | 16 | 1 | >128 | 2 | 0.5 | 8 | — |

Synthetic Methods

The compounds and processes of the present invention will be better understood in connection with the following synthetic schemes which illustrate the methods by which the compounds of the invention may be prepared. The groups R, $R^a$, $R^b$, A, B, D, E, T, Y, and Z are as defined above unless otherwise noted below.

Abbreviations

Abbreviations which have been used in the descriptions of the scheme and the examples that follow are: Ac for acetate; Bz for benzoyl; DBU for 1,8-diazabicyclo[5.4.0]undec-7-ene; DMF for N,N-dimethylformamide; DMSO for dimethylsulfoxide; NMO for N-methylmorpholine-N-oxide; THF for tetrahydrofuran; TMS for trimethylsilyl; TBAC for tetrabutylamminium chloride; 1 8-crown-6 for 1,4,7,10,13,1 6-hexaoxacyclooctadecane;DME for dimethoxyethane; HMPA for hexamethylphosphoramide; NIS for N-iodosuccinimide; NIA for N-iodoacetamide; TFA for trifluoroacetic acid; m-CPBA for meta-chloroperbenzoic acid; DPPA for diphenylphosphoryl azide, Ts for para-toluene sulfonyl; DEAD for diethylazodicarboxylate; and TRIS for tris(hydroxymethyl)aminomethylmethane.

Clarithromycin (3-O-cladinosyl-5-O-desosaminyl-6-O-methyl-erythronolide A) was obtained from Abbott Laboratories. All other starting materials, reagents, and solvents were purchased from Aldrich Chemical Company (Milwaukee, Wi).

Synthetic Methods

The compounds and processes of the present invention will be better understood in connection with the following synthetic schemes, which illustrate the methods by which the compounds of the invention may be prepared. The compounds of formulas (I), (II), and (III) can be prepared by a variety of synthetic routes. Representative procedures are shown in Schemes 1–13. Precursors Ia, IIa, and IIIa, can be converted to compounds of formulas (I), (II), and (III), respectively, by (a) reaction with electrophiles in the presence of base, (b) oxidation, or (c) iodination followed by hydrolysis. Schemes 1–6 and 9–11 illustrate the synthesis of precursors Ia, IIa, and IIIa of the compounds of formula I, II, and III, respectively. Schemes 7 and 8 illustrate the synthesis of diamines and beta amino alcohols which can be used for the synthesis of IIIa. Scheme 12 illustrates the conversion of precursors Ia, IIa, and IIIa to the compounds of the invention. Scheme 13 illustrates the side reactions which can take place during the conversion of precursors Ia, IIa, and IIIa, respectively, to compounds of the invention. In each scheme, the groups R, $R^a$, $R^b$, A, B, D, E, T, Y, and Z are as defined above unless otherwise noted. It will be readily apparent to one of ordinary skill in the art that other compounds within formulas (I)–(III) can be synthesized by substitution of the appropriate reactants and agents in the syntheses shown below. It will also be apparent to one skilled in the art that the selective protection and deprotection steps, as well as order of the steps themselves, can be carried out in varying order, depending on the nature of groups R, $R^a$, $R^b$, A, B, D, E, T, Y, and Z to successfully complete the syntheses of compounds of formulas (I), (II), and (III).

The conversion of erythromycin A to 1 is described in United States patents U.S. Pat. No. 4,990,602; U.S. Pat. No. 4,331,803, U.S. Pat. No. 4,680,368, and U.S. Pat. No. 4,670,549 and European Patent Application EP 260,938, each of which are hereby incorporated by reference. Briefly, the C-9-carbonyl of erythromycin A can be protected as an oxime. Preferred protecting groups at the C-9-carbonyl are =N—O—R or =N—O—C($R^7$)($R^8$)(—O—$R^1$) wherein R is (a) —$C_1$–$C_{12}$-alkyl, (b) —$C_1$–$C_{12}$-alkyl substituted with aryl, (c) —$C_1$–$C_{12}$-alkyl substituted with substituted aryl, (d) =$C_1$–$C_{12}$-alkyl substituted with heteroaryl, (e) —$C_1$–$C_{12}$-alkyl substituted with substituted heteroaryl, (f) $C_3$–$C_{12}$-cycloalkyl, (g) —Si($R^2$)($R^3$)($R^4$) wherein $R^2$, $R^3$ and $R^4$ are each independently —$C_1$–$C_{12}$-alkyl or aryl, and (h) —$(CH_2)_n NR^5 R^6$ wherein n is two to six, and $R^5$ and $R^6$ are independently (i) hydrogen, (ii) —$C_1$–$C_{12}$-alkyl, (iii) —$C_1$–$C_{12}$-alkyl substituted with aryl, (iv) —$C_1$–$C_{12}$-alkyl substituted with substituted aryl, (v) —$C_1$–$C_{12}$-alkyl substituted with heteroaryl, or (vi) —$C_1$–$C_2$-alkyl substituted with substituted heteroaryl, or $R^5$ and $R^6$ taken together with the atom to which they are attached are —$C_3$–$C_{12}$-heterocycloalkyl, and wherein $R^7$ and $R^8$ are independently (a) hydrogen, (b) —$C_1$–$C_{12}$-alkyl, (c) —$C_1$–$C_{12}$-alkyl substituted with aryl, (d) —$C_1$–$C_{12}$-alkyl substituted with substituted aryl, (e) —$C_1$–$C_{12}$-alkyl substituted with heteroaryl or (f) —$C_1$–$C_2$-alkyl substituted with substituted heteroaryl, or $R^7$ and R taken together with the carbon to which they are attached are —$C_3$–$C_{12}$-cycloalkyl. A preferred carbonyl protecting group is O-(1-isopropoxy-cyclohexyl)oxime.

The 2'- and 4"-hydroxy groups of the C-9 protected erythromycin A can be treated with a hydroxy protecting group precursor in an aprotic solvent. Hydroxy protecting group precursors include, acetic anhydride, benzoic anhydride, benzyl chloroformate, hexamethyldisilazane, or a trialkylsilyl halide. Examples of aprotic solvents are dichloromethane, chloroform, THF, N-methyl pyrrolidinone, DMSO, diethylsulfoxide, DMF N,N-dimethylacetamide, hexamethylphosphoric triamide, mixtures thereof, and mixtures of one of these solvents with ether, tetrahydrofuran, 1,2-dimethoxyethane, acetonitrile, ethyl acetate, or acetone. Aprotic solvents do not adversely affect the reaction and are preferably dichloromethane, chloroform, DMF, tetrahydrofuran (THF), N-methyl pyrrolidinone, or mixtures thereof. Protection of the 2'- and 4''-hydroxy groups of the C-9 protected erythromycin A may be accomplished sequentially or simultaneously. Preferred protecting groups include acetyl, benzoyl, and trimethylsilyl. An especially preferred protecting group is trimethylsilyl. A thorough discussion of protecting groups and the solvents in which they are most effective is provided in T.W. Greene and P.G.M. Wuts in Protective Groups in Organic Synthesis, 2nd ed., John Wiley & Son, Inc., 1991, hereby incorporated by reference.

alkylating agents are allyl bromide, propargyl bromide, benzyl bromide, 2-fluoroethyl bromide, 4-nitrobenzyl bromide, 4-chlorobenzyl bromide, 4-methoxybenzyl bromide, a-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, and 1,3-dibromo-1-propene. Examples of alkyl sulfonates are allyl tosylate, 3-phenylpropyl trifluoromethane sulfonate, and n-butylmethanesulfonate. Examples of the solvents used are aprotic solvents such as DMSO, diethylsulfoxide, N,N-dimethylformamide, N,N-dimethylacetamide, N-methyl-2-pyrrolidone, hexamethylphosphoric triamide, mixtures thereof or mixtures of one Scheme 1

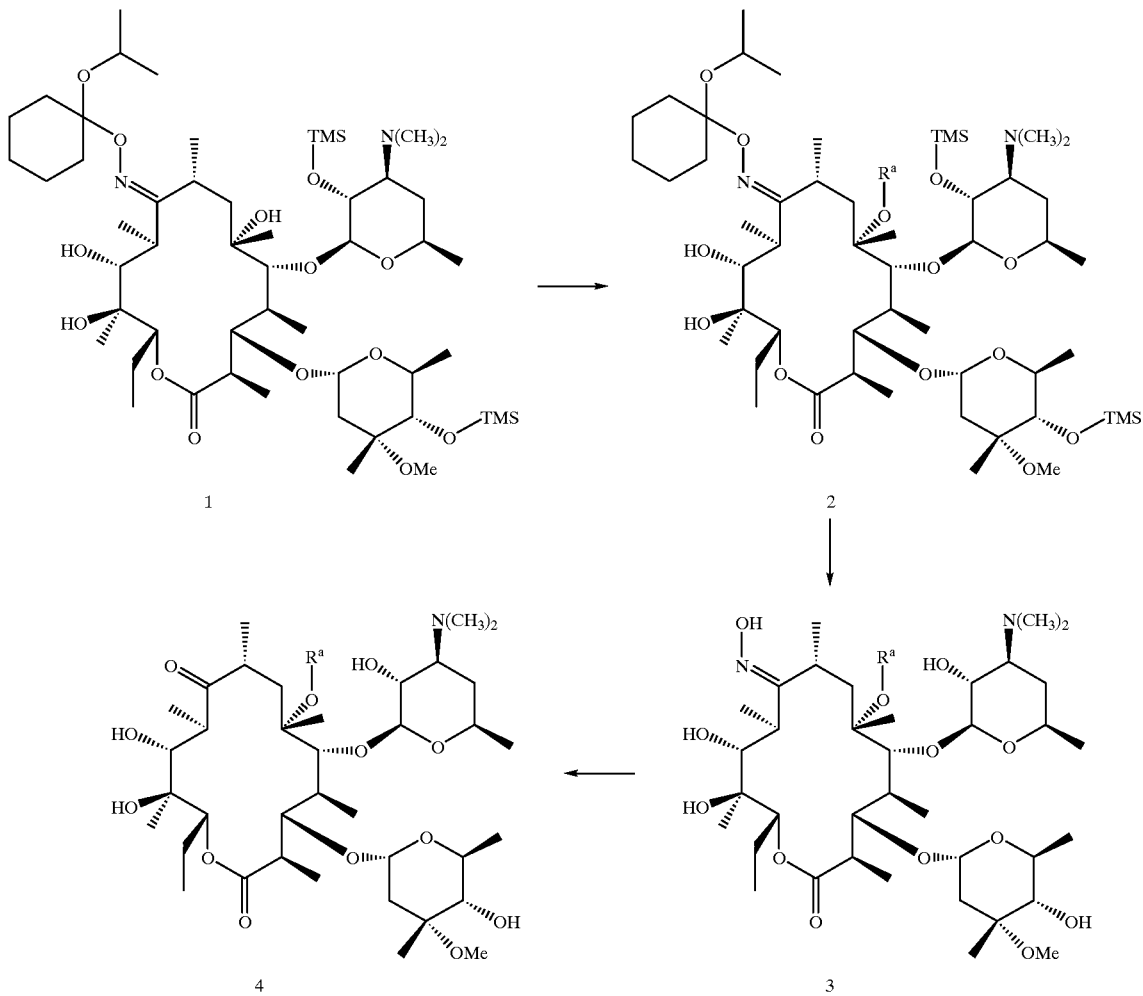

As shown in Scheme 1, conversion of 1 to 2 can be accomplished with an alkylating agent in the presence of base. Alkylating agents include alkyl chlorides, bromides, iodides or alkyl sulfonates. Specific examples of other of these solvents with ether, tetrahydrofuran, 1,2-dimethoxyethane, acetonitrile, ethyl acetate, or acetone. Examples of the base which can be used are potassium hydroxide, cesium hydroxide, tetraalkylammonium hydroxide, sodium hydride, potassium hydride, and alkali metal alkoxides such as potassium isopropoxide, potassium tert-butoxide, and potassium iso-butoxide. An especially preferred method of preparing 2 is treatment of 1 with propargyl bromide in a DMSO/THF mixture with potassium hydroxide as the base. The conversion of 2 to 3 can be accomplished as described in Greene (op. cit.). The preferred conditions for the deprotection of the 2'- and 4"-hydroxyl groups (acetic acid in acetonitrile and water) can result in concomitant removal of the 1-isopropoxycyclohexyl group provide an unalkylated oxime (=N—OH) at C-9. If not, then the conversion can be accomplished in a separate step. The deoximation of 3 to provide 4 can be accomplished as described in Greene (op. cit.). Examples of deoximating agents are nitrous acid (formed in situ by the reaction of sodium nitrite with acids such as HCl, $H_2SO_4$, or TFA) and inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, and potassium metabisulfite in an protic solvent. Exanples of protic solvents are water, methanol, ethanol, propanol, isopropanol, trimethylsilanol, and mixtures thereof. The deoximation reaction can also be accomplished with an organic acid such as formic acid, acetic acid or TFA. The amount of acid used is from about 1 to about 10 equivalents per equivalent of 3. In a preferred embodiment, the deoximation is carried out using sodium nitrite and an inorganic acid such as HCl in ethanol and water to provide the desired 6-O-substituted erythromycin 4 wherein $R^a$ is allyl or propargyl.

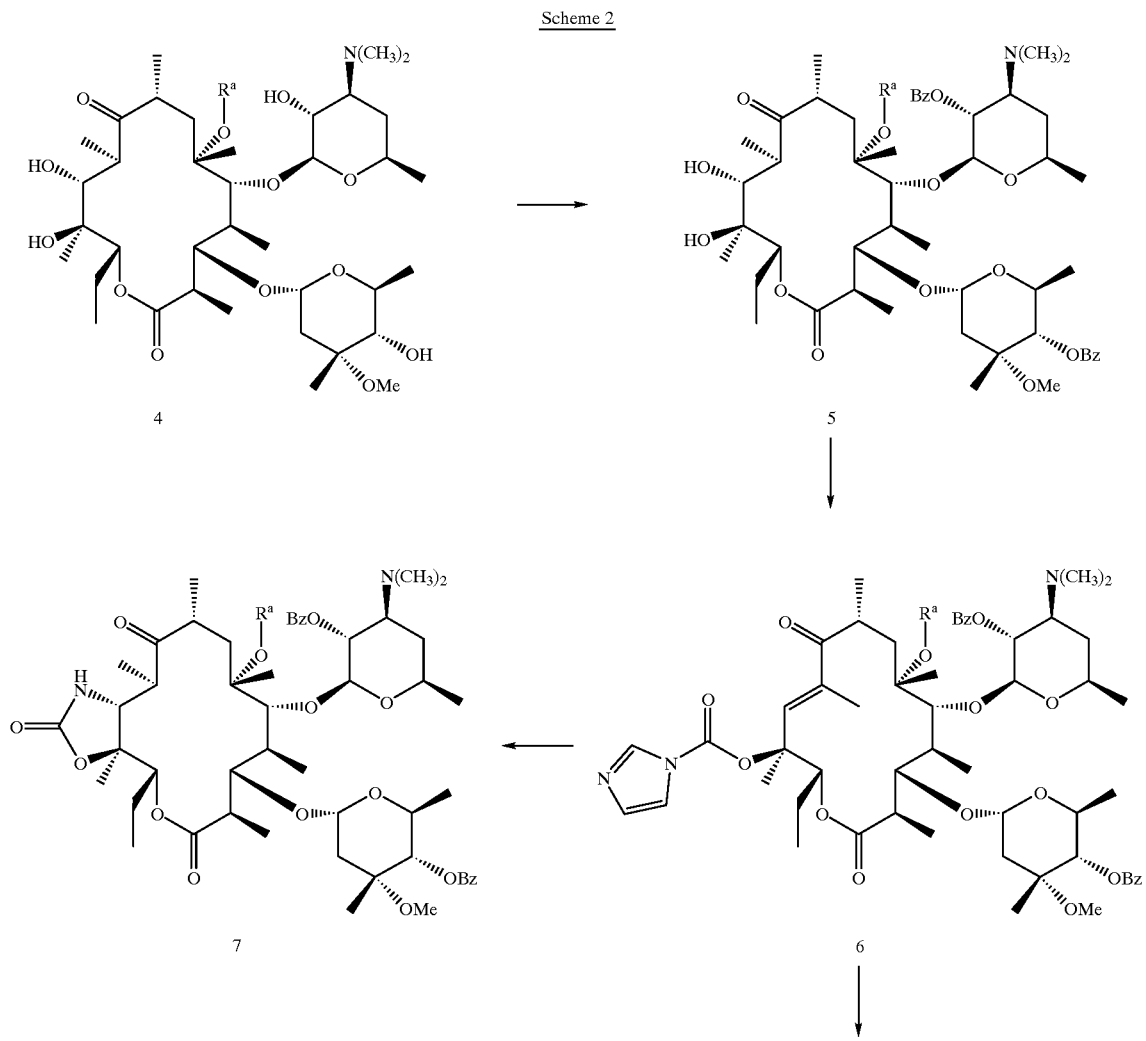

Scheme 2

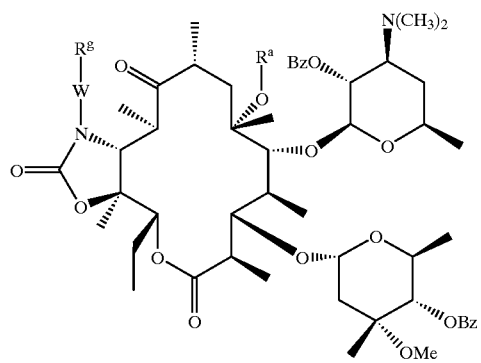

7a

As shown in Scheme 2, conversion of 4 to 5 can be accomplished by the 2'- and 4"-hydroxy group protection procedures described previously. Conversion of 5 to 6 can be accomplished with an excess of an alkali metal hydride or bis(trimethylsilyl)amide in the presence of carbonyldiimidazole in an aprotic solvent for about 8 to about 24 hours at temperature of about −30° C. to about room temperature to provide 6. The alkali metal can be sodium, potassium, or lithium and the aprotic solvent can be one of those defined previously. The reaction can require cooling or heating from about −20° C. to about 70° C., depending on the conditions used, and preferably from about 0° C. to about room temperature. The reaction requires about 0.5 hours to about 10 days, and preferably about 10 hours to 2 days, to complete. Portions of this reaction sequence follow the procedure described by Baker et al., *J. Org. Chem.*, 1988, 53, 2340, incorporated herein by reference. Conversion of 6 to cyclic carbamate 7 (T is —NH—), a precursor of IIa, was accomplished by treatment of 6 with liquid ammonia at room temperature for 20 hours. Alternatively, 6 can be treated with amines of formula $H_2N$—W—$R^g$ such as hydrazines, oximes, and substituted alkylamines to provide precursors of IIa such as 7a, wherein T is —N(W$R^g$)—.

Scheme 3

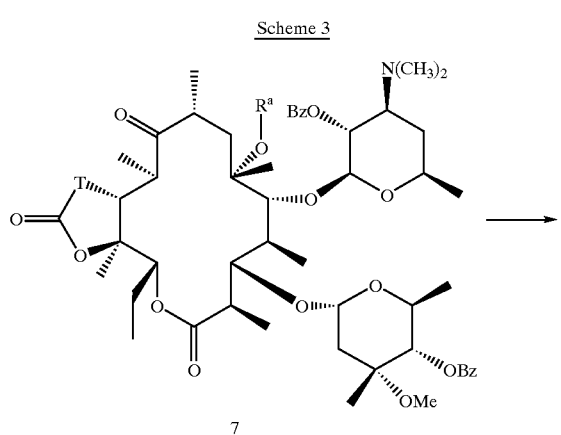

7

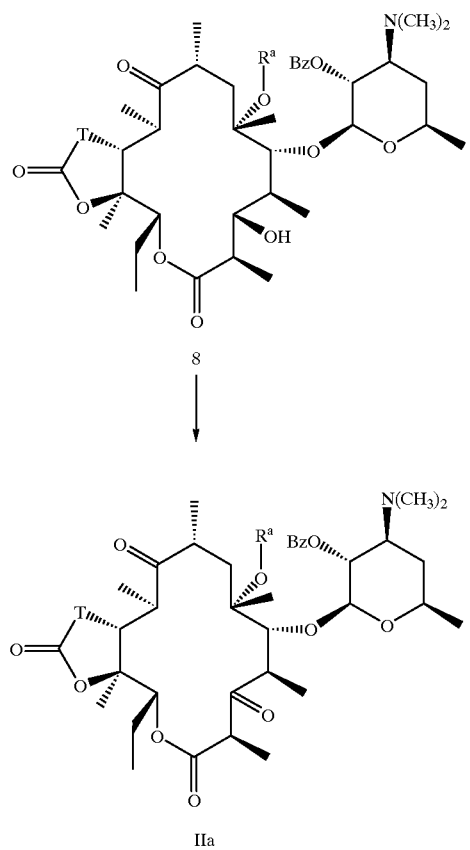

As shown in Scheme 3, 7 can be converted to 8 by hydrolysis of the former with mild aqueous acid or by enzymatic hydrolysis to remove the cladinose moiety from the 3-hydroxy group. Representative acids include dilute hydrochloric acid, sulfuric acid, perchloric acid, chloroacetic acid, dichloroacetic acid, or TFA. Suitable solvents for the reaction include methanol, ethanol, isopropanol, butanol, acetone, and mixtures thereof. Reaction times are typically about 0.5 to about 24 hours. The preferred reaction temperature is about −10° C. to about 60° C., depending on the method chosen. Alternately, 5 can be treated with acid to remove the protected cladinose group from the 3-hydroxy group as described for the conversion of 7 to 8 and treated with base and carbonyldiimidazole then ammonia as described for the conversion of 5 to 6 and the conversion of about −10 to about 25° C. After stirring for about 0.5 to about 4 hours, a tertiary amine such as triethylamine or diisopropylethylamine is added to produce IIa, a precursor to compounds of formula (II).

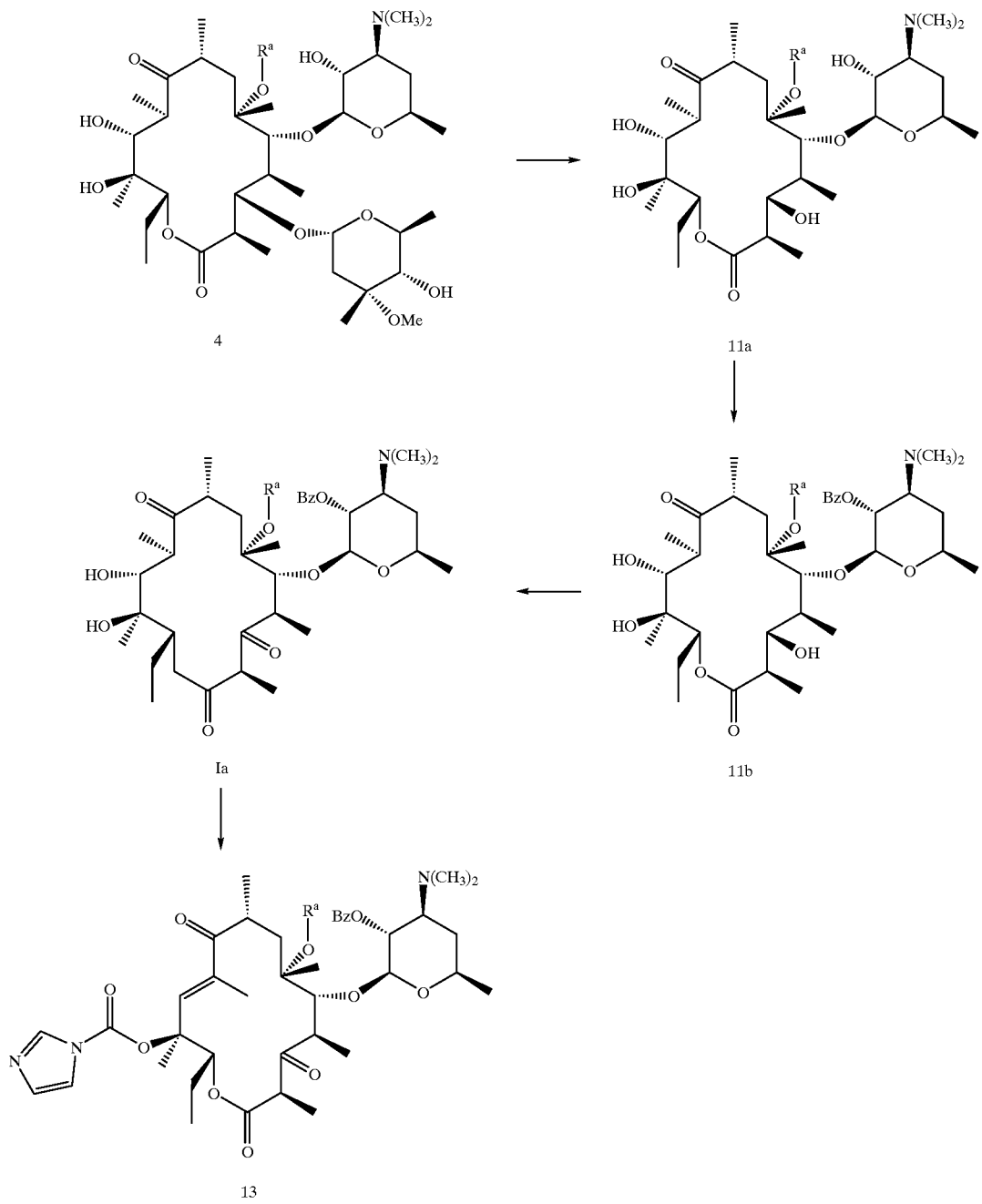

Scheme 4

6 to 7, respectively, to provide 8. The conversion of 8 to Ia can be accomplished by oxidation of the 3-hydroxy group to a 3-oxo group using a Corey-Kim reaction with N-chlorosuccinimide-dimethyl sulfide or with a modified Swern oxidation procedure using a carbodiimide-DMSO complex. In a preferred method, 8 is added to a preformed N-chlorosuccinimide-dimethyl sulfide complex in a chlorinated solvent such as dichloromethane or chloroform at As shown in Scheme 4, 4 (from Scheme 2) can alternatively be (a) treated with acid to remove the cladinose group from the 3-hydroxy group (as described for the conversion of 7 to 8) to provide 11a, (b) protected (as described for the conversion of 4 to 5), to provide 11b, (c) oxidized (as described for the conversion of 8 to 9) to provide Ia, and (d) treated with sodium hydride and carbonyldiimidazole (as described for the conversion of 5 to 6) to provide 13. Alternatively, Ia can be transformed directly to compounds of formula (I) as described in Scheme 9 or transformed to Ia wherein T is —O— by treatment with reagents such as diethylcarbonate or phosgene.

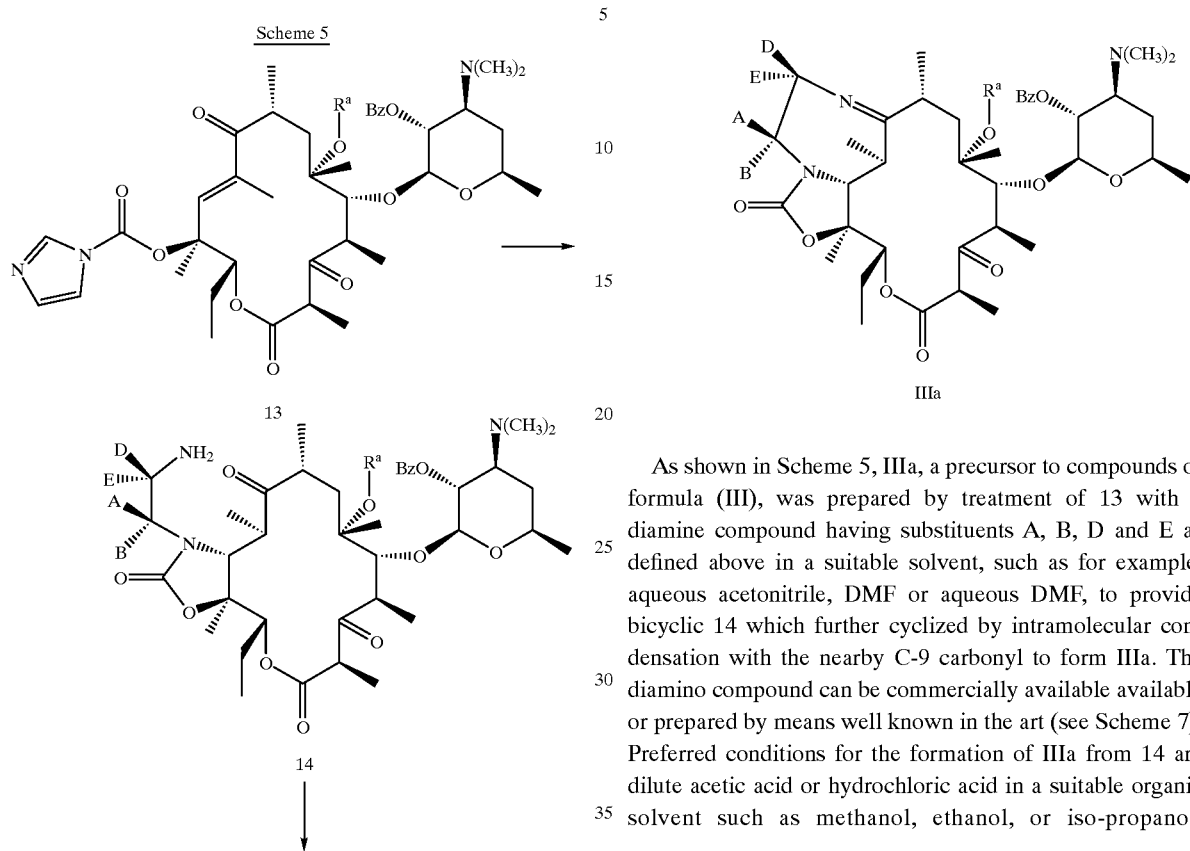

As shown in Scheme 5, IIIa, a precursor to compounds of formula (III), was prepared by treatment of 13 with a diamine compound having substituents A, B, D and E as defined above in a suitable solvent, such as for example, aqueous acetonitrile, DMF or aqueous DMF, to provide bicyclic 14 which further cyclized by intramolecular condensation with the nearby C-9 carbonyl to form IIIa. The diamino compound can be commercially available available or prepared by means well known in the art (see Scheme 7). Preferred conditions for the formation of IIIa from 14 are dilute acetic acid or hydrochloric acid in a suitable organic solvent such as methanol, ethanol, or iso-propanol.

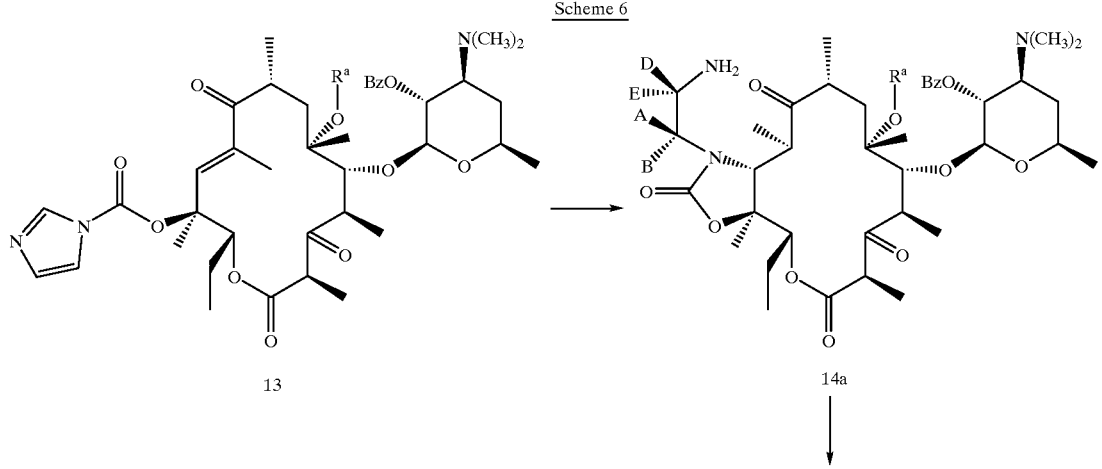

-continued

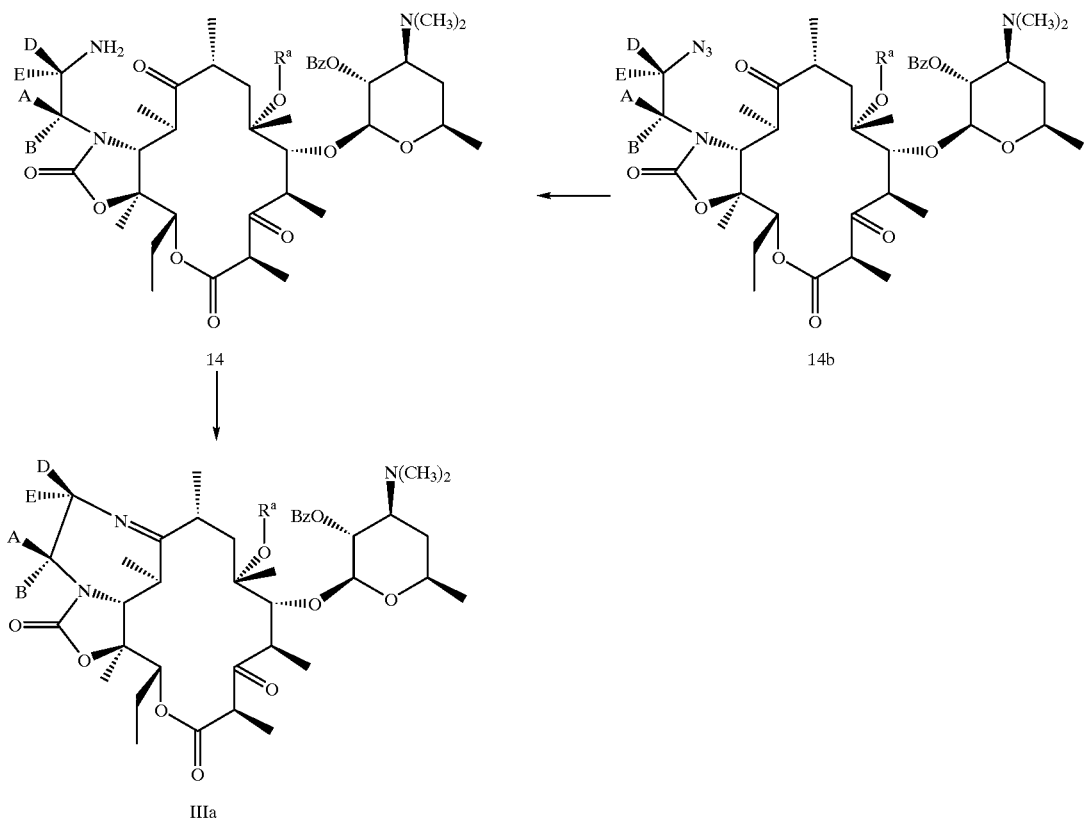

Scheme 6 illustrates an alternative preparation of IIIa. Intermediate 13 from Scheme 4 can be reached with a beta-amino alcohol having substituents A, B, D, and E, as defined above, in a suitable solvent system such as aqueous acetonitrile, DMF or aqueous DMF at from about 0° C. to about 70° C. to provide 14a. The beta amino alcohol can be commercially available or prepared by means well known in the art such as from an amino acid (see Scheme 8). Conversion of 14a to 14b can be achieved with Mitsunobu conditions such as triphenylphosphine, DPPA, and DEAD in tetrahydrofuran. 14b can then be converted to intermediate 14 by treatment of the former with a mild reducing agent such as triphenylphosphine in water, hydrogen with a catalyst, sodium borohydride, or dialkylaluminum hydride. 14 can then be cyclized by treatment with dilute acid, such as acetic acid or HCl, for example, in a suitable organic solvent, such as methanol, ethanol or propanol, for example, for a period of from 4 hours to 10 days, in order to prepare IIIa. Alternatively, the hydroxy group of 14a can be activated by treatment with a sulfonyl chloride, alkyl or aryl sulfonic anhydride or trifluoromethanesufonic anhydride in an aprotic solvent such as diethyl ether, dichloromethane, THF, chloroform, pyridine, or mixtures thereof. The reaction requires cooling or heating, depending on the conditions used. The reaction temperature is preferably about −100° C. to about 10° C. The reaction may require 20 minutes to 24 hours to complete. The activated hydroxy group 14a can then be converted to the amine group of 14b by reacting the former with lithium azide or sodium azide in diethyl ether, dichloromethane, THF, chloroform, pyridine, or mixtures thereof. The reaction temperature is preferably about 0° C. to about 100° C. The azido compound can then be converted to IIa according to the procedures described above.

Scheme 7

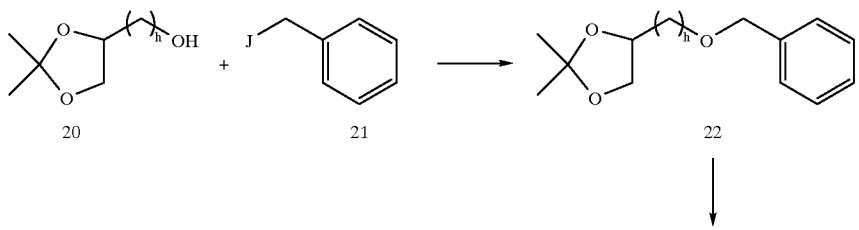

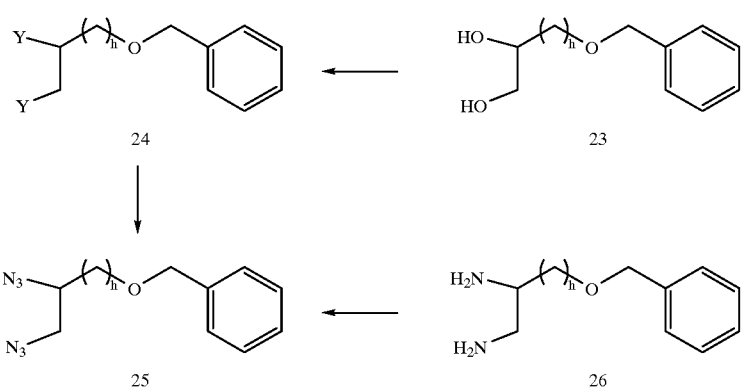

The diamines used for the synthesis of IIIa, described in Scheme 5, can be purchased or prepared by means well known in the art. For example, as shown in Scheme 7, ring 20 can be protected as benzyl ether 22 by treatment of the former with a benzyl halide such as benzyl chloride (J is Cl) or benzyl bromide (J is Br). These compounds can have substituents at positions A, B, D or E in accordance with the desired disposition of substituents on 20 and the chirality of the starting material. Intermediate 20 (h is 1) is available commercially as a pure chiral compound. Intermediate 20 (h is 2) can be prepared as a pure chiral compound by the method of Saito, et al., Tetrahedron, 48:4067 (1992). Intermediate 22 can be hydrolyzed at room temperature in 2/1 (v/v) THF-10% HCl for about one to about four hours to provide 23, which can be treated with a sulfonating agent such as methane sulfonyl chloride or para-toluene sulfonyl chloride to provide 24, wherein Y is a substituted sulfonyl group. Intermediate 24 can then be treated with sodium azide or potassium azide to provide 25. Alternately, the azido compound 25 can be prepared by Mitsunobu reaction of 24 with triphenylphosphine and DPPA-DEAD in tetrahydrofuran. Intermediate 25 can then be reduced to 26 with reducing reagents such as triphenylphosphine-water, hydrogen with a catalyst, sodium borohydride, or dialkylaluminum hydride. Once the diamine has been introduced to 13 (as shown in Scheme 5) to provide IIIa, the benzyl group can be removed by catalytic hydrogenation, and the resulting alcohol can be elaborated to —M—R$^{11}$ by means well known in the art. Alternatively, deprotection of the alcohol and conversion of the alcohol to —M—R$^{11}$ can be performed before attachment of the diamine to 13.

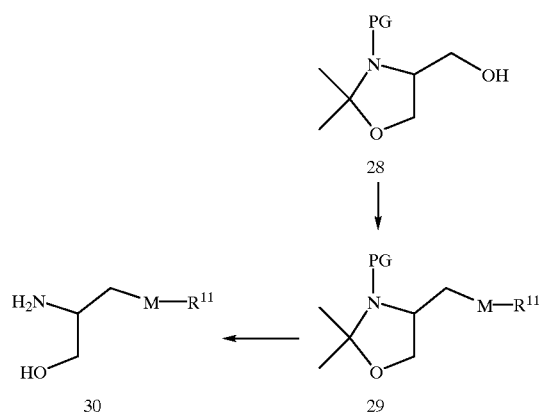

The beta amino alcohols described in Scheme 8 can be purchased or prepared by means well known in the art. A preferred means for the preparation of beta amino alcohols uses amino acids. For example, as shown in Scheme 8, 27 (PG is a nitrogen protecting group, preferably Boc or Cbz) can be prepared from Boc-O-benzyl serine by reduction of the carboxylic acid and treatment of the product with 2-methoxy-1-propene and mild acid, preferably pyridinium para-toluene sulfonate to form the acetonide. Debenzylation of 27 to provide 28 can be achieved with a palladium catalyst, preferably palladium on carbon. Alcohol 28 can then be elaborated to —M—R$^{11}$. Once the desired transformations have been accomplished, the acetonide can be renoved by treatment with acid, preferably dilute HCl, and used to prepare compounds of IIIa as described in Scheme 6.

Scheme 8

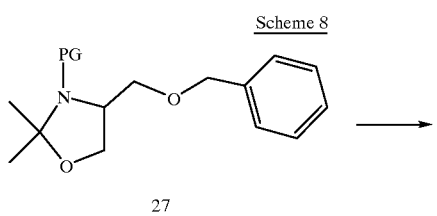

Scheme 9

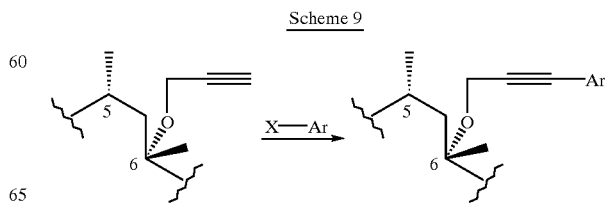

Intermediates wherein $R^a$ is propargyl can be converted to additional intermediates by a number of general routes. A preferred general route is shown in Scheme 9. The 6-O propargyl group can be reacted with groups such as X—Ar wherein Ar is an unsubstituted or a substituted aryl group or heteroaryl group, respectively, and X is one of any number of covalent bond precursors such as halides (preferably bromide and iodide) and sulfonates, to form additional intermediates. The coupling reactions are performed in the presence of Pd(II) or Pd(0) catalysts with promoters such as phosphines (preferably triphenylphosphine), arsines (preferably triphenylarsine), amines (preferably pyridine and triethylamine), and inorganic bases (preferably potassium carbonate or cesium fluoride) in polar, aprotic solvents such as DMF, DMSO, DME, acetonitrile THF, or mixtures thereof at temperatures from about room temperature to about 150° C., depending on the coupling method chosen and the nature of X. A thorough survey of coupling procedures, reagents, and solvents for transition metal-catalyzed couplings is provided in Larock, "Comprehensive Organic Transformations. A Guide to Functional Group Preparations," VCH Publishers, New York (1989), and references therein, and is hereby incorporated by reference.

Scheme 10

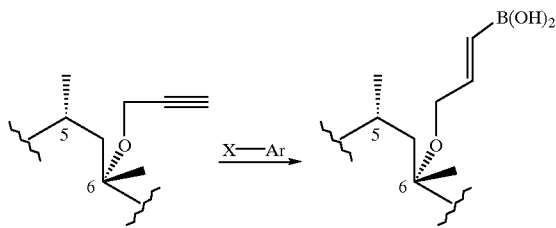

As shown in Scheme 10, propargyl groups can be derivatized with borane-THF in aprotic solvents at temperatures from about −20° C. to about room temperature to provide vinyl boronic acid derivatives. The vinyl boronic acid can then be reacted under Suzuki conditions with X—Ar reagents, catalysts, and promoters described in Scheme 7 to provide additional precursors of compounds of formula (I), (II), and (III). A thorough discussion of Suzuki conditions is provided in Chemical Reviews, 1995, Vol 95, No.7, 2457–2483, incorporated herein by reference.

Scheme 11

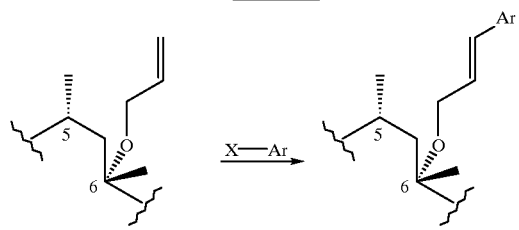

As shown in Scheme 11, compounds wherein $R^a$ is allyl can be coupled to X—Ar reagents under Heck conditions. The synthesis of 6-O-allyl derivatives is described in United States patent U.S. Pat. No. 5,866,549, Example 1 steps 1a–g and Example 102, steps 120a–c, incorporated herein by reference. A thorough discussion of Heck conditions is provided in U.S. Pat. No. 5,866,549, incorporated herein by reference.

Scheme 12

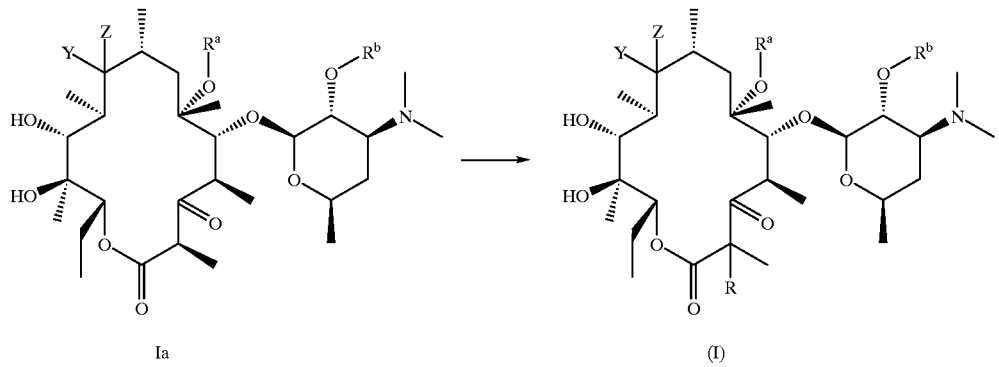

Ia       (I)

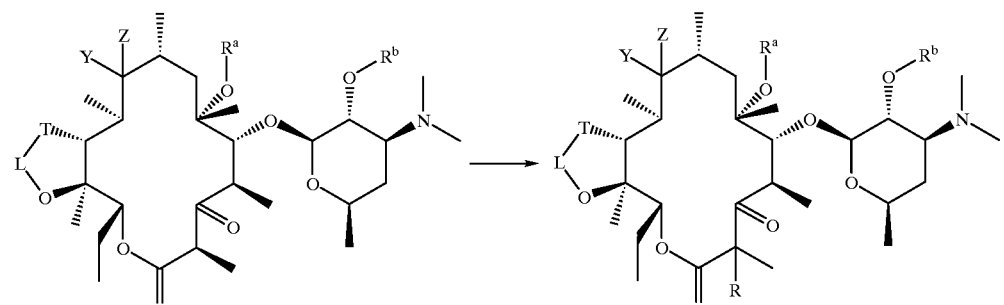

IIa        (II)

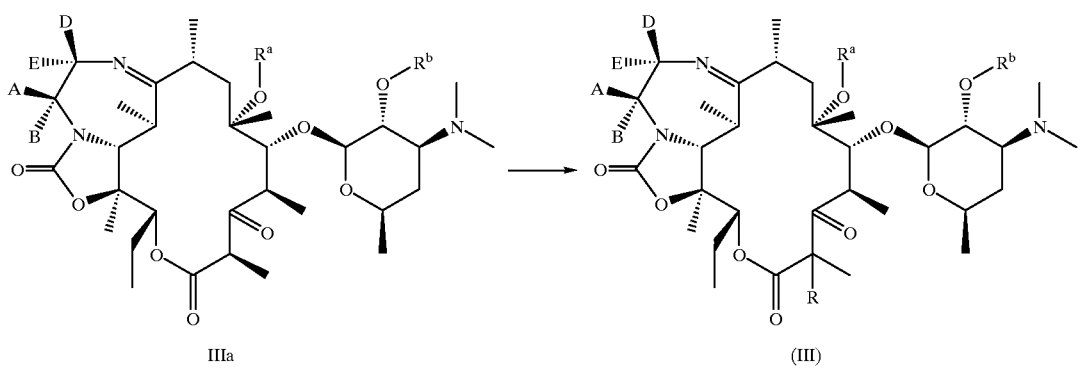

IIIa        (III)

Scheme 12 shows the preparation of compounds of formulas (I), (II), and (III) from the immediate precursors Ia, IIa, and IIIa, respectively. Conversion of compounds of formulas Ia, IIa, and IIIa to compounds of formulas (I), (II), and (III), can be accomplished with (a) electrophiles in the presence of base (b) oxidation, or (c) iodination followed by hydrolysis.

Electrophiles include alkyl chlorides, bromides, iodides, sulfonates, and sulfonic anhydrides. Specific examples of alkylating agents are allyl bromide, propargyl bromide, benzyl bromide, 2-fluoroethyl bromide, 4-nitrobenzyl bromide, 4-chlorobenzyl bromide, 4-methoxybenzyl bromide, a-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, and 1,3-dibromo-1-propene. Examples of alkyl sulfonates are allyl tosylate, 3-phenylpropyl trifluoromethane sulfonate, and n-butylmethanesulfonate. Examples of sulfonic anhydrides are methyl and ethyl sulfonic anhydride. Examples of electrophilic nitrogen reagents include $ClNH_2$, $(C_6H_5)_2P(O)NH_2$, $Br_2/NaN_3$, and $TsN_3$.

Examples of bases which can be used for electrophilic addition are sodium hydride, potassium hydride, potassium carbonate, alkali metal alkoxides such as potassium isopropoxide, potassium tert-butoxide, and potassium isobutoxide, lithium bis(trimethylsilyl)amide, sodium bis(trimethylsilyl)amide, potassium bis(trimethylsilyl)amide, and lithium diisopropylamide.

Examples of oxidizing agents include include $OsO_4$, and NMO, $RuO_4$, and m-CPBA. Examples of the solvents used for the electrophilic additions or oxidations are aprotic solvents such as DMSO, THF, DME, diethylsulfoxide, N,N-dimethylformamide, N,N-dimethylacetamide, N-methyl-2-pyrrolidone, HMPA, or mixtures thereof.

Examples of iodinating agents are NIS and water, NIA and water, and iodine and water. Examples of the solvents used for the electrophilic additions or oxidations are aprotic solvents such as DMSO, THF, DME, diethylsulfoxide, N,N-dimethylformamide, N,N-dimethylacetamide, N-methyl-2-pyrrolidone, HMPA, or mixtures thereof.

Examples of the solvents used for the electrophilic additions or oxidations, or iodination/hydrolysis are aprotic solvents such as DMSO, THF, DME, diethylsulfoxide, N,N-dimethylformamide, N,N-dimethylacetamide, N-methyl-2-pyrrolidone, HMPA, or mixtures thereof.

Scheme 13

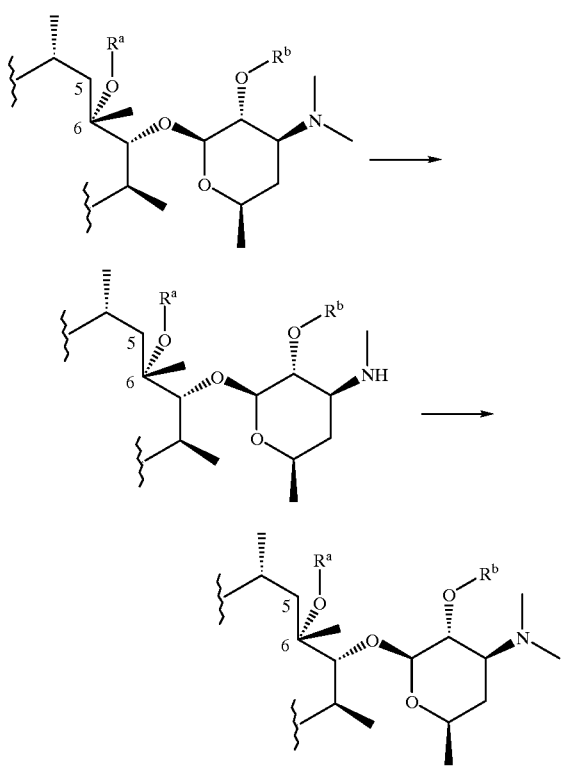

As shown in Scheme 13, treatment of Ia, IIa, or IIIa with NIS and hydrolysis can result in concomitant desmethylation of the 2'-dimethylamino group. Reintroduction of the methyl group can be accomplished by any number of means well known in the art. A preferred method is sequential treatment of the product with formaldehyde and a reducing agent such as sodium borohydride or sodium cyanoborohydride.

The compounds and processes of the present invention will be better understood in connection with the following examples, which are intended as an illustration of and not a limitation upon the scope of the invention.

EXAMPLE 1

Compound of formula (II): $R^a$ is $CH_3$, $R^b$ is H, Y and Z together are O, T is —NH—, R is —$CH_2CH$=$CH$-(phenyl)

Step 1a:

A suspension of clarithromycin (900 g, 1.2 mole) in water (10.8 L) and ethanol (4.0 L), was stirred at room temperature until homogeneous (about 20 minutes), treated with 1M HCl (2.16 L) over 15 minutes, stirred for 20 hours, treated with 2.00 M NaOH (1.20 L) over 30 minutes until pH 10.5–11.0, stirred for 2 hours, and filtered. The precipitate was collected, washed with cold water, and dried under vacuum at 50° C. to provide 601 g of the title compound.

MS m/z 590 (M+H)$^+$.

Step 1b:

The product from Step 1a (600 g, 1.01 mol) in dichloromethane (2.0 L) was treated sequentially with 90% technical grade benzoic anhydride (380 g, 1.59 mol) and triethylamine (222 mL, 1.59 mol) over 10 minutes, stirred for 48 hours, treated with saturated sodium bicarbonate solution (1.5 L), and stirred for 30 minutes. The layers were separated, and the organic layer was washed sequentially with water (3×600 mL) and brine (600 mL), dried ($Na_2SO_4$) and filtered, and concentrated. The resulting syrup was triturated with a warm solution of hexane (2.0 L) and ethyl acetate (100 mL) to provide white crystals. The product was filtered, washed with hexane and dried in a vacuum oven for is hours at ambient temperature to provide 691 g of the desired product.

MS m/z 694 (M+H)$^+$.

Step 1c:

A slurry of N-chlorosuccinimide (57.0 g, 0.42 mol) in anhydrous dichloromethane (600 mL) at 0° C. was treated dropwise over 30 minutes with dimethyl sulfide (36.0 mL, 0.49 mol) and dropwise over 45 minutes with the compound from Step 1b (200.0 g, 0.29 mol) in dichloromethane (1.20 L), stirred for 30 minutes, treated dropwise with a solution of triethylamine (40.0 mL) in dichloromethane (200 mL) over 30 minutes, washed with saturated aqueous $NaHCO_3$, (3×600 mL) and brine (600 mL), dried ($Na_2SO_4$), filtered, and concentrated to provide a thick syrup, which solidified on standing. The solid was crushed and dried ofor 18 hours at ambient temperature in a vacuum oven to provide 196 g of the desired product.

MS m/z 692 (M+H)$^+$.

Step 1d:

A solution of the product from from Step 1c (20.00 g, 28.9 mmol) in pyridine (40 mL) at 0° was treated with methanesulfonic anhydride (14.6 g, 83.81 mmol), stirred at room temperature for 17 hours, and concentrated. The concentrate was dissolved in ethyl acetate (400 mL), washed sequentially with saturated aqueous $NaHCO_3$, water, and brine, dried ($MgSO_4$), decolorized with charcoal, filtered through diatomaceous earth, and concentrated to provide 24.46 g the crude product which was used in the next step without further purification.

Step 1e:

A solution of the product from Step 1d in acetone (70 mL) at room temperature was treated with DBU (5.22 mL, 34.9 mmol), stirred for 22 hours, and concentrated. The residue was dissolved in ethyl acetate, (250 mL), washed sequentially with saturated aqueous $NaHCO_3$ (2×100 mL), water, and brine, dried ($MgSO_4$), decolorized with charcoal, filtered through diatomaceous earth, and concentrated. The concentrate was purified by flash chromatography on silica gel with 40% ethyl acetate/hexanes containing 0.25 % concentrated ammonium hydroxide to provide the desired product.

MS m/z 674 (M+H)$^+$.

Step 1f:

Dry NaH (1.05 g, 26.3 mmol) was mixed with THF (90 mL), cooled to 0° C., treated with the product from Step 1e (8.40 g, 12.5 mmol) over one minute, stirred for 15 minutes, treated over 15 minutes with a solution of 1.1'-carbonyldiimidazole (5.98 g, 36.9 mmol) in THF (60 mL) via cannula, stirred for 5 hours, treated with 5% $KH_2PO_4$ solution, stirred at 0° C. for 20 minutes, and extracted with ethyl acetate. The extract was washed with brine, dried ($Na_2SO_4$), filtered, and concentrated. The concentrate was purified by flash chromatography on silica gel with with a gradient of from 25% acetone/hexanes to 40% acetone/hexanes to provide the desired product.

MS m/z 768 (M+H)$^+$;

$^1$H NMR (CDCl$_3$): δ 0.90 (t, 3H), 0.95 (d, 3H), 1.21 (d, 3H), 1.27 (d, 3H), 1.32 (s, 3H), 2.25 (s, 6H), 2.78 (s, 3H), 2.97 (m, 1H), 3.58 (m, IH), 2.63 (q, 1H), 4.14 (d, 1H), 4.50 (d, 1H), 5.00 (dd, 1H), 5.65 (dd, 1H), 6.75 (s, 1H), 7.05 (m, 1H), 7.35 (m, 1H), 7.43 (dd, 2H), 7.54 (t, 1H), 8.02 (d, 2H), 8.07(s, 1H);

$^{13}$C NMR (CDCl$_3$): δ 204.8, 168.8, 165.0, 145.9, 138.4, 138.1, 137.0, 132.7, 130.8, 130.5, 129.7, 128.2, 117.0, 102.1, 84.5, 81.0, 78.5, 76.9, 72.0, 69.2, 63.7, 50.9, 50.2, 47.2, 40.7, 40.3, 38.8, 31.1, 30.8, 22.5, 20.9, 20.7, 20.0, 18.8, 14.8, 14.2, 13.2, 10.4.

Step 1g:

A solution of a sample of the the product from Step 1f (134 mg, 0.179 mmol) in acetonitrile (4 mL) at −78° C. was treated with liquid ammonia for 6 minutes, stirred at room temperature for 24 hours, concentrated first by evaporation of the ammonia at room temperature and atmospheric pressure, and then by removal of the acetonitrile. The concentrate was purified by flash chromatography on silica gel with a gradient of from 3:7 acetone/hexanes to 1:1 acetone/hexanes to provide 30.6 mg of the desired product.

MS m/z 717 (M+H)$^+$.

Step 1h:

A slurry of the product from Step 1g (717 mg, 1.0 mmol) and NaH (80% in mineral oil, 36 mg, 1.2 mmol) in DMF (5 mL) was stirred at room temperature for 10 minutes, warmed to 60° C. for 30 miniutes, cooled to −30° C., treated dropwise with cinnamyl bromide (167 μL, 1.2 mmol) stirred for 6 hours at room temperature, treated with ethyl acetate, washed with 5% Na$_2$CO$_3$ and brine, dried (Na$_2$SO$_4$), filtered, and concentrated. The concentrate was purified by flash column chromatography with 50:50:1:0.1 hexane/ethyl acetate/methanol/ammonium hydroxide to provide 600 mg of the desired product.

MS m/z 833 (M+H)$^+$.

Step 1i:

A solution of the product from Step 1h in methanol was stirred at reflux for or 24 hours and concentrated. The concentrate was purified by flash column chromatography to provide of the desired product.

MS m/z 729 (M+H)$^+$.

EXAMPLE 2

Compound of formula (II): R$^a$ is CH$_3$, R$^b$ is H, Y and Z together are O, T is —N(W(R$^g$))—, W is —(CH$_2$)$_p$—, p is 4, R$^g$ is phenyl, R is —OH Step 2a: Compound of formula (II): R$^a$ is CH$_3$ R$^b$ is H, Y and Z together are O, T is —N(W(R$^g$))—, W is —(CH$_2$)$_p$—, p is 4, R is phenyl, R is hydrogen This precursor compound was prepared as described in FR 2669337, Example 10, Stage B.

MS m/z 849 (M+H)$^+$.

Step 2b:

A solution of the product from Step 2a (5.0g, 5.9 mmol) and NMO (1.38 g, 11.8 mmol) in THF (25 mL) was treated with OsO$_4$ (4% in water, 0.090 mL 0.0147 mmol), stirred at at room temperature for 24 hours, treated with tert-butanol, stirred for 4 hours, treated with NMO (2.8 g, 23.9 mmol), stirred for 5 days, treated with NMO (2.8 g, 23.9 mmol) and OsO$_4$ (0.25 mL, 0.04 mmol), stirred for 18 hours, treated sequentially with water and NaHSO$_3$ (10 g), stirred for 18 hours, treated with ethyl acetate, washed sequentially with saturated NaHCO$_3$ (2×), water, and brine, dried (Na$_2$SO$_4$), filtered, and concentrated. The concentrate was purified by flash column chromatography on silica gel with a gradient of from 50:50:1 hexane/ethyl acetete/ammonium hydroxide to 40:60:1 hexane/ethyl acetete/ammonium hydroxide to provide 2.23 g of the desired product.

MS m/z 761 (M+H)$^+$.

Step 2c:

A solution of the product from Step 2b (100 mg) in methanol (5 mL) was stirred at reflux for 24 hours and concentrated. The concentrate was purified by flash column chromatography on silica gel with 97.2:1.8:1 chloroform/methanol/ammonium hydroxide to provide 78 mg of the desired product.

MS m/z 681 (M+H)$^+$.

EXAMPLE 3

Compound of formula (II): R$^a$ is —CH$_2$CH(OH)CH$_2$OH, R$^b$ is H, Y and Z together are O, T is —NH—, R is —OH Step 3a: Compound of formula (II): R$^a$ is —CH$_2$CH=CH$_2$, R$^b$ is H, Y and Z together are O, T is —NH—, R is hydrogen This precursor compound was prepared as described in U.S. Pat. No. 5,866,549, Example 177, Steps 177a–e.

MS m/z 681 (M+H)$^+$.

Step 3b:

A solution of the product from Step 3a (1.0 g, 1.47 mmol) and NMO (1.2 g, 10.2 mmol) in THF at room temperature was treated with OsO$_4$, stirred for 18 hours, treated sequentially with NaHSO$_3$ (200 mg) and water, stirred for 20 minutes, treated with ethyl acetate, washed sequentially with water and brine, dried (Na$_2$SO$_4$), filtered, and concentrated to provide the desired product which was used in the next step without further purification.

MS m/z 731 (M+H)$^+$.

Step 3c:

A solution of the product from Step 3b (160 mg) in methanol (5 mL) was stirred at room temperature for 24 hours and concentrated to provide 119 mg of the desired product.

MS m/z 689 (M+H)$^+$.

EXAMPLE 4

Compound of formula (II): R$^a$ is —CH$_2$CH=CH-(3-quinolinyl), R$^b$ is H, Y and Z together are O, T is —NH—, R is —CH$_2$CH=CH$_2$ Step 4a: Compound of formula (II): R$^a$ is —CH$_2$CH=CH-(3-quinolinyl), R$^b$ is H, Y and Z together are O, T is —NH—, R is hydrogen This precursor compound was prepared as described in U.S. Pat. No. 5,866,549, Example 178, Steps 178a and b.

MS m/z 766 (M+H)$^+$.

Step 4b:

A solution of the product from Step 4a (153 mg, 0.2 mmol) in 1:1 THF/DMSO (10 mL) at 0° C. was treated sequentially with allyl bromide and a solution of 1M potassium tert-butoxide in THF (0.4 mL, 0.4 mmol) in 1:1 THF/DMSO (4 mL), stirred for 2 hours, treated with allyl bromide (4 mL), stirred for 30 minutes, treated with ethyl acetate (40 mL), washed sequentially with saturated NaHCO$_3$ and brine, dried (Na$_2$SO$_4$), filtered, and concentrated. The concentrate was purified by flash column chromatography on silica gel with 95:5:0.5 dichloromethane/methanol/ammonium hydroxide to provide 18 mg of the desired product.

MS m/z 806 (M+H)$^+$.

EXAMPLE 5

Compound of formula (II): R$^a$ is —CH$_2$CH=CH-(3-quinolinyl), R$^b$ is H, Y and Z together are O, T is —NH—, R is —CH$_2$CH$_2$CO$_2$C$_2$H$_5$, A solution of the product from Step 4a (153 mg, 0.2 mmol) and 18-crown-6 in DME (10 mL) at 0° C. was treated sequentially dropwise with 0.5M potassium bis(hexamethylsilyl)amide in toluene (0.48 mL, 0.240 mmol) and 2-bromoethyl acetate, stirred for 2 hours, treated with 5% NaHCO$_3$ and extracted with ethyl acetate. The extract was washed with brine, dried (Na$_2$SO$_4$), filtered, and concentrated. The concentrate was purified by flash column chromatography on silica gel with 50:50:1 acetone/hexane/triethylamine to provide 49 mg of the desired product.

MS m/z 852 (M+H)$^+$.

EXAMPLE 6

Compound of formula (III): R$^a$ is CH$_3$, R$^b$ is H, Y and Z tozether are O, A is —CH$_2$O, B, D, and E are H, R is —CH$_2$-(4-chlorophenyl)

Step 6a: Compound of formula (III): R$^a$ is CH$_3$, R$^b$ is H, Y and Z together are O, A is —CH$_2$OH, B, D, and E are H, R is H This precursor compound was prepared as described in PCT application WO 98/3054-A1, Example 62, Steps 62a–f and Example 63.

Step 6b:

A solution of the product from Step 6a (43 mg, 55.7 µmol in THF at 0° C. was treated with NaH (60% in mineral oil, 14.5 mg, 111 mmol), stirred for 15 minutes at 0° C. and at room temperature for 15 minutes, treated sequentially with 1-(bromomethyl)-4-chlorobenzene (23 mg, 111 µmol) and DMF 300 µL), stirred at room temperature for 1.5 hours, cooled to 0° C., treated sequentially with acetic acid (3 mL) and benzylamine (50 µL), stirred at room temperature for 15 minutes, treated with dichloromethane, washed sequentially with water (2×) and brine, dried (Na$_2$SO$_4$), filtered, and concentrated. The concentrate was purified by flash column chromatography with a gradient of from 1:1 diethyl ether/hexane to 1:1 acetone/hexane to 3:1 acetone/hexane to provide 24 mg of a 1.3:1 mixture of diastereomers at C-2.

MS m/z 896 (M+H)$^+$.

Step 6c:

A solution of the product from Step 6b (24 mg) in methanol (5 mL) was stirred at reflux for 24 hours and concentrated. The concentrate was purified by flash column chromatography with 5% methanol/dichloromethane to provide 18 mg of the desired product.

MS m/z 792 (M+H)$^+$.

EXAMPLE 7

Compound of formula (I): R$^a$ is CH$_3$, R$^b$ is —C(O)C$_6$H$_5$, Y and Z together are O, R is —OH A solution of the product from Example 1, Step 1c (5.0 g, 7.23 mmol) and NMO (1.7 g, 14.5 mmol) in THF (25 mL) was treated with OsO$_4$ (4% in water, 0.090 mL 0.0147 mmol), stirred at at room temperature for 24 hours, treated sequentially with NMO (1.7 g, 1.45 mmol) and OsO$_4$ (0.10 mL), stirred for 48 hours at room temperature, treated with water (2 mL), stirred for 20 minutes to provide a two-phase mixture, treated with tert- butanol, stirred for 4 hours, treated with NMO (3.4 g, 29 mmol), stirred for 5 days, treated with NMO (3.4 g, 29 mmol) and OsO$_4$ (0.25 mL, 0.04 mmol), stirred for 10 days, treated sequentially with water and NaHSO$_3$ (10 g), stirred for 18 hours, treated with ethyl acetate, washed sequentially with saturated NaHCO$_3$ (2×), water, and brine, dried (Na$_2$SO$_4$), filtered, and concentrated. The concentrate was purified by flash column chromatography on silica gel with a gradient of from. 50:50:1 hexane/ethyl acetete/ammonium hydroxide to 40:60:1 hexane/ethyl acetete/ammonium hydroxide to provide 2.23 g of the desired product.

MS m/z 708 (M+H)$^+$.

EXAMPLE 8

Compound of formula (II): R$^a$ is —CH$_2$CH=CH-(3-quinolinyl), R$^b$ is H, Y and Z together are O, T is —NH—, R is —OH, Step 8a:

A solution of the product from Example 4, Step 4a (9.44g mg, 12.34 mmol) in acetonitrile at 0° C. was treated with N-iodosuccinimide over 30 minutes, warmed to room temperature for 18 hours, cooled to 0° C., treated with additional, N-iodosuccinimide (0.666 g, 2.96 mmol), stirred for 2 hours, and concentrated. The concentrate was treated with ethyl acetate, washed sequentially with 5% NaHCO$_3$, water, and brine, dried (Na$_2$SO$_4$), filtered, and concentrated. A portion of the concentrate (800 mg) was purified by flash column chromatography on silica gel with a gradient of from 95:5:0.5 to 90:10:0.5 dichloromethane/methanol/ammonium hydroxide to provide 105 mg of the desired product.

MS m/z 768 (M+H)$^+$.

Step 8b:

A solution of the product from Step 8a (50 mg, 0.065 mmol) in methanol (1 mL) at room temperature was treated sequentially with formaldehyde (37% in water, 50 µL, 0.650 mmol) acetic acid (12 µL, 0.650 mmol), and NaBH$_3$CN (10 mg, 0.150 mmol), stirred for 4 hours, treated with ethyl acetate, washed sequentially with 5% NaHCO$_3$, water, TRIS, and brine, dried (Na$_2$SO$_4$), filtered, and concentrated. The concentrate was purified by flash column chromatography on silica gel with a gradient of from 95:5:0.5 to 90:10:0.5 dichloromethane/methanol/ammonium hydroxide to provide 30.2 mg of the desired product.

MS m/z 782 (M+H)$^+$.

EXAMPLE 9

Compound of formula (II): R$^a$ is —CH$_2$C=CH, R$^b$ is H, Y and Z together are O, T is —NH—, R is —CH$_2$CH=CH-(phenyl)

Step 9a: Compound of formula (II): R$^a$ is —CH$_2$C≡CH R$^b$ is H, Y and Z together are O, T is —NH—, R is H This precursor compound was prepared as described in U.S. Pat. No. 5,866,549, Example 246, Steps 246a–h.

Step 9b:

A solution of the product from Step 9a (250 mg, 0.369 mmol) in DMF (2.5 mL) at room temperature was treated sequentially with K$_2$CO$_3$ (76 mg, 0.553 mmol), TBAC (10 mg, 0.037 mmol), CuCl (3.6 mg, 0.037 mmol) and cinnamyl chloride (68 µL, 0.479 mmol), stirred for 18 hours, treated with 1:1 ethyl acetate/diethyl ether, washed sequentially with 5% NaHCO$_3$, water, and brine, dried (MgSO$_4$), filtered, and concentrated. The concentrate was purified by flash column chromatography on silica gel with 1 % methanol/dichloromethane containing 1% ammonium hydroxide to provide 41 mg of the desired product.

MS m/z 796 (M+H)$^+$.

Step 9c:

A solution of the product from Step 9b (41 mg) in methanol (1 mL) was stirred at room temperature for 24 hours and concentrated to provide 33 mg of the desired product.

MS m/z 753 (M+H)$^+$.

EXAMPLE 10

Compound of formula (II): $R^a$ is $CH_3$, $R^b$ is H, Y and Z together are O, T is —N(W($R^g$))—, W is —$(CH_2)_p$—, p is 4, g is phenyl, R is —OH Step 10a:
Dry NaH (426 mg, 17.8 mmol) was mixed with THF (75 mL), cooled to 0° C., treated with the product from Example 1, Step 1e (5.02 g, 7.46 mmol), stirred for 30 minutes, treated over 15 minutes with methanesulfonic anhydride, stirred at room temperature for 4.5 hours, treated with 5% $KH_2PO_4$, and extracted with ethyl acetate. The extract was washed sequentially with 5% $NaHCO_3$, water, and brine, dried ($MgSO_4$), filtered, and concentrated. The concentrate was purified by flash column chromatography on silica gel with 2:1:1 hexane:acetone:dichloromethane to provide 3.72 g of the desired product.

Step 10b:
The product from Step 10a (1.00 g, 1.33 mmol) was processed as described in Step 1f and purified by flash column chromatography on silica gel with 1:1 hexane:acetone:to provide 1.12 g the desired product.
MS m/z 846 (M+H)$^+$.

Step 10c:
The product from Step 10b (315 mg, 0.373 mmol) in acetonitrile (1 mL) was treated with 4-phenyl-1-butanamine (0.3 mL), warmed to 50° C. for 6 hours, cooled to room temperature, treated with dichloromethane, washed with 5% $KH_2PO_4$ and brine, dried ($MgSO_4$), filtered, and concentrated. The concentrate was purified by flash column chromatography on silica gel with 15% acetone/hexane to provide 212 mg of the desired product.
MS m/z 927 (M+H)$^+$.

Step 10d:
A solution of the product from Step 10c (200 mg) in methanol (10 mL) was stirred at room temperature for 24 hours and concentrated. The concentrate was purified by flash column chromatography on silica gel with a gradient of from 5% to 10% methanol/dichloromethane containing 0.1% ammonium hydroxideto provide 171 mg of the desired product.
MS m/z 823 (M+H)$^+$.

EXAMPLE 11

Compound of formula (II): $R^a$ is $CH_3$, $R^b$ is H, Y and Z together are O, T is —N(W($R^g$))—, W is —$(CH_2)_p$—, p is 2, R is amino, R is —$SO_2CH_3$ Step 11a:
The product from Example 10, Step 10b (400 mg, 0.473 mmol) in acetonitrile (3 mL) was treated with 1,2-ethanediamine (3 mL, 45 mmol), stirred for 18 hours, treated with dichloromethane, washed with 5% $KH_2PO_4$ and brine, dried ($Na_2SO_4$), filtered, and concentrated. The concentrate was purified by flash column chromatography on silica gel with 4% methanol/dichloromethane containing 1% ammonium hydroxide to provide 272 mg of the desired product.
MS m/z 838 (M+H)$^+$.

Step 11b:
A solution of the product from Step 11b (205 mg) in methanol (10 mL) was stirred at room temperature for 24 hours and concentrated. The concentrate was purified by flash column chromatography on silica gel with a gradient of from 5% methanol/dichloromethane to 10% methanol/dichloromethane containing 0.2% ammonium hydroxideto provide 171 mg of the desired product.
MS m/z 823 (M+H)$^+$.

EXAMPLE 12

Compound of formula (II): $R^a$ is $CH_3$ $R^b$ is H, Y and Z together are O, T is —NH—, R is —$CH_2CH$=$CH_2$ Step 12a:
The product from Example 1, Step 1g was processed as described in Example 4, Step 4b to provide the desired product.

Step 12b:
The product from Step 12a in methanol was stirred at reflux for 24 hours and concentrated to provide the desired product.
MS m/z 653 (M+H)$^+$.

EXAMPLE 13

Compound of formula (II): $R^a$ is $CH_3$, $R^b$ is H, Y and Z together are O, T is —NH—, R is —$CH_2CH_3$ Step 13a:
The product from Example 1, Step 1g was processed as described in Example 4, Step 4b (substituting 1-bromoethane for allyl bromide) to provide the desired product.

Step 13b:
The product from Step 13a in methanol was stirred at reflux for 24 hours and concentrated to provide the desired product.
MS m/z 641 (M+H)$^+$.

EXAMPLE 14

Compound of formula (II): $R^a$ is $CH_3$, $R^b$ is H, Y and Z together are O, T is —NH—, R is —$CH_2CO_2CH_3$ Step 14a:
The product from Example 1, Step 1g was processed as described in Example 4, Step 4b (substituting methyl 2-bromoacetate for allyl bromide) to provide the desired product.

Step 14b:
The product from Step 14a in methanol was stirred at reflux for 24 hours and concentrated to provide the desired product.
MS m/z 685 (M+H)$^+$.

EXAMPLE 15

Compound of formula (II): $R^a$ is $CH_3$, $R^b$ is H, Y and Z together are O, T is —NH—, R is —$CH_2CH_2CO_2CH_3$ Step 15a:
The product from Example 1, Step 1g was processed as in Example 4, Step 4b (substituting methyl 3-bromopropanoate for allyl bromide) to provide the desired product.

Step 15b:
The product from Step 15a in methanol was stirred at reflux for 24 hours and concentrated to provide the desired product.
MS m/z 699 (M+H)$^+$.

EXAMPLE 16

Compound of formula (II): $R^a$ is $CH_3$, $R^b$ is H, Y and Z together are O, T is —NH—, R is —$CH_2$C(O)(phenyl)

Step 16a:
The product from Example 1, Step 1g was processed as described in Example 4, Step 4b (substituting 2-bromo-1-phenyl-1-ethanone for allyl bromide) to provide the desired product.

Step 16b:
The product from Step 16a in methanol was stirred at reflux for 24 hours and concentrated to provide the desired product.
MS m/z 731 (M+H)$^+$.

EXAMPLE 17

Compound of formula (II): $R^a$ is $CH_3$, $R^b$ is H, Y and Z together are O, T is —NH—, R is benzyl Step 17a:
The product from Example 1, Step 1g was processed as described in Example 4, Step 4b (substituting 1-(bromomethyl)benzene for allyl bromide) to provide the desired product.

Step 17b:
The product from Step 17a in methanol was stirred at reflux for 24 hours and concentrated to provide the desired product.
MS m/z 703 (M+H)$^+$.

EXAMPLE 18

Compound of formula (II): $R^a$ is $CH_3$, $R^b$ is H, Y and Z together are O, T is —NH—, R is —$CH_2$-(4-tert-butyl-phenyl)

Step 18a:
The product from Example 1, Step 1g was processed as described in Example 4, Step 4b (substituting 1-(bromomethyl)-4-(tert-butyl)benzene for allyl bromide) to provide the desired product.

Step 18b:
The product from Step 18a in methanol was stirred at reflux for 24 hours and concentrated to provide the desired product.
MS m/z 759 (M+H)$^+$.

EXAMPLE 19

Compound of formula (II): $R^a$ is $CH_3$, $R^b$ is H, Y and Z together are O, T is —NH—, R is —1,1'-biphenyl-2-ylmethyl Step 19a:
The product from Example 1, Step 1g was processed as described in Example 4, Step 4b (substituting 3-(bromomethyl)-1,1'-biphenyl for allyl bromide) to provide the desired product.

Step 19b:
The product from Step 19a in methanol was stirred at reflux for 24 hours and concentrated to provide the desired product.
MS m/z 779 (M+H)$^+$.

EXAMPLE 20

Compound of formula (II): $R^a$ is $CH_3$, $R^b$ is H, Y and Z together are O, T is —NH—, R is —$CH_2$-(3-chlorophenyl)

Step 20a:
The product from Example 1, Step 1g was processed as described in Example 4, Step 4b (substituting 1-(bromomethyl)-3-chlorobenzene for allyl bromide) to provide the desired product.

Step 20b:
The product from Step 20a in methanol was stirred at reflux for 24 hours and concentrated to provide the desired product.
MS m/z 737 (M+H)$^+$.

EXAMPLE 21

Compound of formula (II): $R^a$ is $CH_3$ $R^b$ is H, Y and Z together are O, T is —NH—, R is —$CH_2CH_2$CH=CH-(phenyl)

Step 21a:
The product from Example 1, Step 1g was processed as described for the product from Example 4, Step 4a in Example 4, Step 4b (substituting 1-[(E)-3-bromo-1-propenyl]benzene for allyl bromide) to provide the desired product.

Step 21b:
The product from Step 21a in methanol was stirred at reflux for 24 hours and concentrated to provide the desired product.
MS m/z 743 (M+H)$^+$.

EXAMPLE 22

Compound of formula (II): $R^a$ is $CH_3$, $R^b$ is H, Y and Z together are O, T is —NH—, R is —$CH_2$-(3-naphthyl)

Step 22a:
The product from Example 1, Step 1g was processed as described in Example 4, Step 4b (substituting 2-(bromomethyl)naphthalene for allyl bromide) to provide the desired product.

Step 22b:
The product from Step 22a in methanol was stirred at reflux for 24 hours and concentrated to provide the desired product.
MS m/z 753 (M+H)$^+$.

EXAMPLE 23

Compound of formula (II): $R^a$ is $CH_3$, $R^b$ is H, Y and Z together are O, T is —NH—, R is —$CH_2$-(9-anthracenyl)

Step 23a:
The product from Example 1, Step 1g was processed as described in Example 4, Step 4b (substituting 9-(bromomethyl)anthracene for allyl bromide) to provide the desired product.

Step 23b:
The product from Step 23a in methanol was stirred at reflux for 24 hours and concentrated to provide the desired product.
MS m/z 803 (M+H)$^+$.

EXAMPLE 24

Compound of formula (II): $R^a$ is $CH_3$, $R^b$ is H, Y and Z together are O, T is —NH—, R is —$CH_2$-(4-fluorophenyl)

Step 24a:

The product from Example 1, Step 1g was processed as described in Example 4, Step 4b (substituting 1-(bromomethyl)-4-fluorobenzene for allyl bromide) to provide the desired product.

Step 24b:

The product from Step 24a in methanol was stirred at reflux for 24 hours and concentrated to provide the desired product.

MS m/z 721 (M+H)$^+$.

What is claimed is:

1. A compound selected from the group consisting of a compound of formula (I)

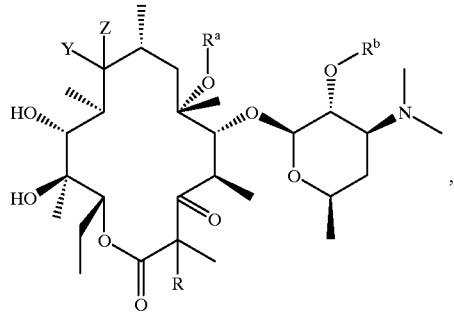

a compound of formula (II)

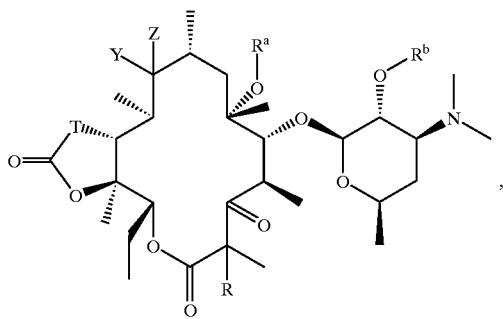

and a compound of formula (III)

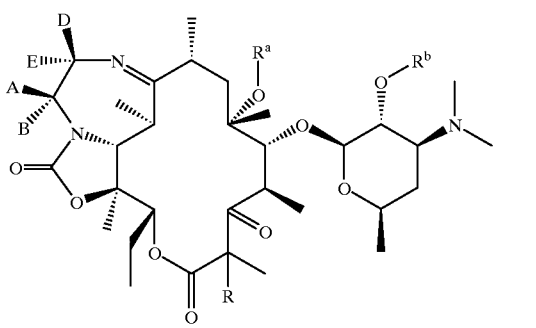

and pharmaceutically acceptable salts, esters, and prodrugs thereof wherein, in formulas (I)–(III), Y and Z together are selected from the group consisting of
(1) oxo,
(2) =N—OH,
(3) =N—OR$^1$ wherein R$^1$ is selected from the group consisting of
  (a) —C$_1$–C$_{12}$-alkyl,
  (b) —C$_1$–C$_{12}$-alkyl substituted with aryl,
  (c) —C$_1$–C$_{12}$-alkyl substituted with substituted aryl,
  (d) —C$_1$–C$_{12}$-alkyl substituted with heteroaryl,
  (e) —C$_1$–C$_{12}$-alkyl substituted with substituted heteroaryl,
  (f) —C$_3$–C$_{12}$-cycloalkyl,
  (g) —Si(R$^2$)(R$^3$)(R$^4$), wherein R$^2$, R$^3$, and R$^4$, are each independently —C$_1$–C$_{12}$- alkyl or aryl, and
  (h) —(CH$_2$)$_n$NR$^5$R$^6$ wherein n is two to six, and R$^5$ and R$^6$ are independently selected from the group consisting of
    (i) hydrogen,
    (ii) —C$_1$–C$_{12}$-alkyl,
    (iii) —C$_1$–C$_{12}$-alkyl substituted with aryl,
    (iv) —C$_1$–C$_{12}$-alkyl substituted with substituted aryl,
    (v) —C$_1$–C$_{12}$-alkyl substituted with heteroaryl, and
    (vi) —C$_1$–C$_{12}$-alkyl substituted with substituted heteroaryl,
  or
  R$^5$ and R$^6$ taken together with the atom to which they are attached are C$_3$–C$_{12}$-heterocycloalkyl,
and
(4) =N—OC(R$^7$)(R$^8$)(—OR$^1$), wherein R$^1$ is defined above, and R$^7$ and R$^8$ are independently selected from the group consisting of
  (i) hydrogen,
  (ii) —C$_1$–C$_{12}$-alkyl,
  (iii) —C$_1$–C$_{12}$-alkyl substituted with aryl,
  (iv) —C$_1$–C$_{12}$-alkyl substituted with substituted aryl,
  (v) —C$_1$–C$_{12}$-alkyl substituted with heteroaryl, and
  (vi) —C$_1$–C$_{12}$-alkyl substituted with substituted heteroaryl,
or
R$^7$ and R$^8$ taken together with the atom to which they are attached are C$_3$–C$_{12}$-cycloalkyl,
or
one of Y and Z is hydrogen, and the other is selected from the group consisting of (1) hydrogen,
(2) hydroxy,
(3) —OR$^1$ wherein R$^1$ is defined above, and
(4) —NR$^5$R$^6$ wherein R$^5$ and R$^6$ are defined above;

T is selected from the group consisting of
(1) —O—,
(2) —NH—, and
(3) —N(W(R$^g$))— wherein W is absent or selected from the group consisting of
  (a) —O—,
  (b) —(CH$_2$)$_p$— wherein p is one to six, and
  (c) —NH—,
and
R$^g$ is selected from the group consisting of
  (a) hydrogen,
  (b) —C$_3$–C$_7$-cycloalkyl,
  (c) aryl,
  (d) substituted aryl,
  (e) heteroaryl,
  (f) substituted heteroaryl,
  (g) —C$_1$–C$_6$-alkyl,
  (h) —NR$^5$R$^6$ wherein R$^5$ and R$^6$ are defined above, and
  (i) —C$_1$–C$_6$-alkyl substituted with one or more substituents independently selected from the group consisting of
    (i) aryl,
    (ii) substituted aryl,
    (iii) heteroaryl,
    (iv) substituted heteroaryl,
    (v) hydroxy,
    (vi) —OR$^1$, and
    (vii) —NR$^5$R$^6$ wherein R$^5$ and R$^6$ are defined above;

R$^a$ is selected from the group consisting of
(1) —C$_1$–C$_{10}$-alkyl optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein R$^1$ is defined above,
  (i) cyano,
  (j) —S(O)$_q$R$^1$ wherein R$^1$ is defined above and q is zero to two,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and
  (u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
  (a) halogen,
  (b) carboxaldehyde,
  (c) —CO$_2$R$^1$ wherein R$^1$ is defined above,
  (d) —C(O)R$^1$ wherein R$^1$ is defined above,
  (e) —C(O)NR$^5$R$^6$ wherein R$^5$ and R$^6$ are defined above,
  (f) cyano,
  (g) aryl,
  (h) substituted aryl,
  (i) heteroaryl, and
  (j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein R$^1$ is defined above,
  (i) cyano,
  (j) —S(O)$_q$R$^1$ wherein R$^1$ and q are defined above,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and
  (u) =NNHC(O)NR$^5$R$^6$ wherein R$^5$ and R$^6$ are defined above;

R$^b$ is hydrogen or a hydroxy protecting group;
R is selected from the group consisting of
(1) —C$_1$–C$_{10}$-alkyl optionally substituted with one or more substituents independently selected from the group consisting of
  (a) halogen,
  (b) hydroxy,
  (c) —OR$^1$,
  (d) oxo,
  (e) —NR$^5$R$^6$ wherein R$^5$ and R$^6$ are defined above,
  (f) —CO$_2$R$^1$ wherein R$^1$ is defined above,
  (g) —C(O)NR$^5$R$^6$ wherein R$^5$ and R$^6$ are defined above,
  (h) =N—OR$^1$ wherein R$^1$ is defined above,
  (i) cyano,
  (j) —S(O)$_q$R$^1$ wherein R$^1$ and q are defined above,
  (k) aryl,
  (l) substituted aryl,
  (m) heteroaryl,
  (n) substituted heteroaryl,
  (o) heterocycloalkyl,
  (p) substituted heterocycloalkyl,
  (q) —NHC(O)R$^1$ wherein R$^1$ is defined above,
  (r) —NHC(O)NR$^5$R$^6$ wherein R$^5$ and R$^6$ are defined above,
  (s) =NNR$^5$R$^6$ wherein R$^5$ and R$^6$ are defined above,
  (t) =NNHC(O)R$^1$ wherein R$^1$ is defined above, and (u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
(a) halogen,
(b) carboxaldehyde,
(c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl,
(5) —C$_4$–C$_{10}$-alkynyl,
wherein (4) and (5) can be optionally substituted with one or more substituents independently selected from the group consisting of
(a) halogen,
(b) hydroxy,
(c) —OR$^1$ wherein R$^1$ is defined above,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) S(O)$_q$R— wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;
(6) —C(O)R$^1$ wherein R$^1$ is defined above,
(7) —C(O)OR$^1$ wherein R$^1$ is defined above,
(8) —C(O)NR$^5$R$^6$ wherein R$^5$ and R$^6$ are defined above,
(9) hydroxyl,
(10) —OR$^1$ wherein R$^1$ is defined above,
(11) —NR$^5$R$^6$ wherein R$^5$ and R$^6$ are defined above, and
(12) —SO$_2$R$^1$ wherein R$^1$ is defined above;
and
A, B, D, and E are independently selected from the group consisting of
(1) hydrogen, and
(2) —C$_1$–C$_6$-alkyl optionally substituted with one or more substituents selected from the group consisting of
(a) —M—R$^{11}$ wherein M is selected from the group consisting of
(i) a covalent bond,
(ii) —C(O)NH—,
(iii) —NHC(O)—,
(iv) —NH—,
(v) —N(CH$_3$)—,
(vi) —O—,
(vii) —S(O)$_n$— wherein n is defined above,
(viii) —C(=NH)NH—,
(ix) —C(O)O—,
(x) —OC(O)—,
(xi) —OC(O)NH—,
(xii) —NHC(O)O—, and
(xiii) —NHC(O)NH—,
and
R$^{11}$ is selected from the group consisting of
(i) —C$_1$–C$_6$-alkyl optionally substituted with a substituent selected from the group consisting of
(1') aryl,
(2') substituted aryl,
(3') heteroaryl, and
(4') substituted heteroaryl,
(ii) aryl,
(iii) substituted aryl,
(iv) heteroaryl,
(v) substituted heteroaryl and
(vi) heterocycloalkyl,
(b) aryl,
(c) substituted aryl,
(d) heteroaryl,
(e) substituted heteroaryl,
(i) heterocycloalkyl,
(g) hydroxy,
(h) —C$_1$–C$_6$-alkoxy,
(i) halo, and
(j) —NR$^{15}$R$^{16}$ wherein R$^{15}$ and R$^{16}$, together with the nitrogen atom to which they are attached, are a 3- to 7-membered ring optionally containing therein a moiety selected from the group consisting of
(i) —O—,
(ii) —NH—,
(iii) —N(C$_1$–C$_6$-alkyl)—,
(iv) —N(C$_1$–C$_6$-alkyl-substituted with aryl)—,
(v) —N(C$_1$–C$_6$-alkyl substituted with substituted aryl)—,
(vi) —N(C$_1$–C$_6$-alkyl substituted with heteroaryl)—,
(vii) —N(C$_1$–C$_6$-alkyl substituted with substituted heteroaryl)—,
(viii) —S—, and
(ix) —S(O)$_q$— wherein q is defined above,
or
any one pair of substituents selected from the group consisting of AB, AD, AE, BD, BE, and DE, taken together with the atom or atoms to which they are attached, are C$_3$–C$_7$-cycloalkyl or a four- to seven-membered ring containing a moiety selected from the group consisting of
(1) —O—,
(2) —NH—,
(3) —N(C$_1$–C$_6$-alkyl)—,
(4) —N(C$_1$–C$_6$-alkyl substituted with aryl)—,
(5) —N(C$_1$–C$_6$-alkyl substituted with substituted aryl)—,
(6) —N(C$_1$–C$_6$-alkyl substituted with heteroaryl)—,
(7) —N(C$_1$–C$_6$-alkyl substituted with substituted heteroaryl)—, and
(8) —S(O)$_q$— wherein q is defined above.

2. A compound according to claim 1 wherein R$^a$ is CH$_3$, R$^b$ is —C(O)C$_6$H$_5$, Y and Z together are O, and R is —OH.

3. A compound according to claim 1 wherein T is —NH— or —N(W(R$^g$))— wherein W and R$^g$ are defined above.

4. A compound according to claim 3 wherein W is —(CH$_2$)$_p$— and R$^g$ is phenyl or amino.

5. A compound according to claim 4 wherein $R^g$ is phenyl.
6. A compound according to claim 4 wherein $R^g$ is amino.
7. A process for the preparation of
a compound of formula (I)

(I)
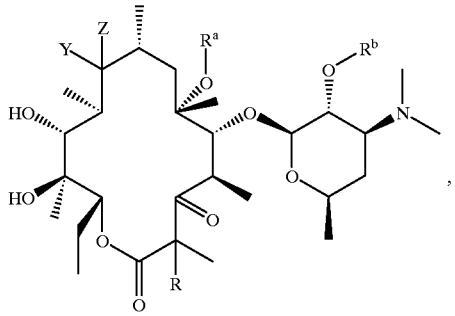

a compound of formula (II)

(II)
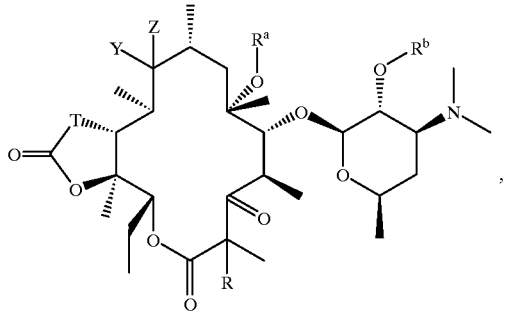

and
a compound of formula (III)

(III)
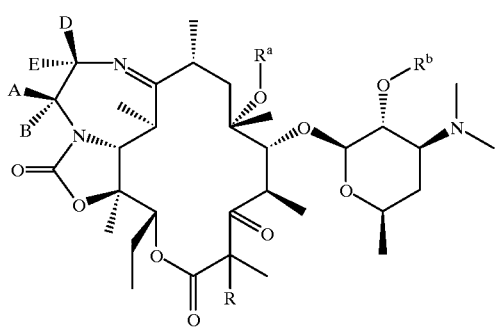

wherein, in formulas (I)–(III),
Y and Z together are selected from the group consisting of
(1) oxo,
(2) =N—OH,
(3) =N—$OR^1$ wherein $R^1$ is selected from the group consisting of
  (a) —$C_1$–$C_{12}$-alkyl,
  (b) —$C_1$–$C_{12}$-alkyl substituted with aryl,
  (c) —$C_1$–$C_{12}$-alkyl substituted with substituted aryl,
  (d) —$C_1$–$C_{12}$-alkyl substituted with heteroaryl,
  (e) —$C_1$–$C_{12}$-alkyl substituted with substituted heteroaryl,
  (f) —$C_3$–$C_{12}$-cycloalkyl,
  (g) —Si($R^2$)($R^3$)($R^4$), wherein $R^2$, $R^3$, and $R^4$, are each independently —$C_1$–$C_{12}$-alkyl or aryl, and
  (h) —$(CH_2)_n NR^5 R^6$ wherein n is two to six, and $R^5$ and $R^6$ are independently selected from the group consisting of
    (i) hydrogen,
    (ii) —$C_1$–$C_{12}$-alkyl,
    (iii) —$C_1$–$C_{12}$-alkyl substituted with aryl,
    (iv) —$C_1$–$C_{12}$-alkyl substituted with substituted aryl,
    (v) —$C_1$–$C_{12}$-alkyl substituted with heteroaryl, and
    (vi) —$C_1$–$C_{12}$-alkyl substituted with substituted heteroaryl,
    or
    $R^5$ and $R^6$ taken together with the atom to which they are attached are $C_3$–$C_{12}$-heterocycloalkyl,
  and
(4) =N—OC($R^7$)($R^8$)(—$OR^1$), wherein $R^1$ is defined above, and $R^7$ and $R^8$ are independently selected from the group consisting of
  (i) hydrogen,
  (ii) —$C_1$–$C_{12}$-alkyl,
  (iii) —$C_1$–$C_{12}$-alkyl substituted with aryl,
  (iv) —$C_1$–$C_{12}$-alkyl substituted with substituted aryl,
  (v) —$C_1$–$C_{12}$-alkyl substituted with heteroaryl, and
  (vi) —$C_1$–$C_{12}$-alkyl substituted with substituted heteroaryl,
  or
  $R^7$ and $R^8$ taken together with the atom to which they are attached are $C_3$–$C_{12}$-cycloalkyl,
or
one of Y and Z is hydrogen, and the other is selected from the group consisting of
(1) hydrogen,
(2) hydroxy,
(3) —$OR^1$ wherein $R^1$ is defined above, and
(4) —$NR^5 R^6$ wherein $R^5$ and $R^6$ are defined above;
T is selected from the group consisting of
(1) —O—,
(2) —NH—, and
(3) —N(W($R^g$))— wherein W is absent or selected from the group consisting of
  (a) —O—,
  (b) —$(CH_2)_p$— wherein p is one to six, and
  (c) —NH—,
and
$R^g$ is selected from the group consisting of
(a) hydrogen,
(b) —$C_3$–$C_7$-cycloalkyl,
(c) aryl,
(d) substituted aryl,
(e) heteroaryl,
(f) substituted heteroaryl,
(g) —$C_1$–$C_6$-alkyl,
(h) —$NR^5 R^6$ wherein $R^5$ and $R^6$ are defined above, and
(i) —$C_1$–$C_6$-alkyl substituted with one or more substituents independently selected from the group consisting of
  (i) aryl,
  (ii) substituted aryl,
  (iii) heteroaryl,
  (iv) substituted heteroaryl,
  (v) hydroxy, (vi) —OR$^1$, and
(vii) —NR$^5$R$^6$ wherein R$^5$ and R$^6$ are defined above;
R$^a$ is selected from the group consisting of
(1) —C$_1$–C$_{10}$-alkyl optionally substituted with one or more substituents independently selected from the group consisting of
(a) halogen,
(b) hydroxy,
(c) —OR$^1$,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ is defined above and q is zero to two,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
(a) halogen,
(b) carboxaldehyde,
(c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl, and
(5) —C$_4$–C$_{10}$-alkynyl,
wherein (4) and (5) can be optionally substituted with one or more substituents independently selected from the group consisting of
(a) halogen,
(b) hydroxy,
(c) —OR$^1$,
(d) oxo,
(e) —NR$^5$R$^6$ wherein R$^5$ and R$^6$ are defined above,
(f) —CO$_2$RI wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;
R$^b$ is hydrogen or a hydroxy protecting group;
R is selected from the group consisting of
(1) —C$_1$–C$_{10}$-alkyl optionally substituted with one or more substituents independently selected from the group consisting of
(a) halogen,
(b) hydroxy,
(c) —OR ,
(d) oxo,
(e) —NR$^5$R$^6$ wherein R$^5$ and R$^6$ are defined above,
(f) —CO$_2$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl,
(n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above,
(2) —C$_3$-alkenyl,
(3) —C$_3$-alkynyl,
wherein (2) and (3) can be optionally substituted with a substituent selected from the group consisting of
(a) halogen,
(b) carboxaldehyde,
(c) —CO$_2$R$^1$ wherein R$^1$ is defined above,
(d) —C(O)R$^1$ wherein R$^1$ is defined above,
(e) —C(O)NR$^5$R$^6$ wherein R$^5$ and R$^6$ are defined above,
(f) cyano,
(g) aryl,
(h) substituted aryl,
(i) heteroaryl, and
(j) substituted heteroaryl,
(4) —C$_4$–C$_{10}$-alkenyl,
(5) —C$_4$–C$_{10}$-alkynyl,
wherein (4) and (5) can be optionally substituted with one or more substituents independently selected from the group consisting of
(a) halogen,
(b) hydroxy,
(c) —OR$^1$ wherein R$^1$ is defined above,
(d) oxo,
(e) —NR$^5$R$^6$ wherein R$^5$ and R$^6$ are defined above,
(f) —C$_{12}$R$^1$ wherein R$^1$ is defined above,
(g) —C(O)NR$^5$R$^6$ wherein R$^5$ and R$^6$ are defined above,
(h) =N—OR$^1$ wherein R$^1$ is defined above,
(i) cyano,
(j) —S(O)$_q$R$^1$ wherein R$^1$ and q are defined above,
(k) aryl,
(l) substituted aryl,
(m) heteroaryl, (n) substituted heteroaryl,
(o) heterocycloalkyl,
(p) substituted heterocycloalkyl,
(q) —NHC(O)R$^1$ wherein R$^1$ is defined above,
(r) —NHC(O)NR$^5$R$^6$ wherein R$^5$ and R$^6$ are defined above,
(s) =NNR$^5$R$^6$ wherein R$^5$ and R$^6$ are defined above,
(t) =NNHC(O)R$^1$ wherein R$^1$ is defined above, and
(u) =NNHC(O)NR$^5$R$^6$ wherein R$^5$ and R$^6$ are defined above;
(6) —C(O)R$^1$ wherein R$^1$ is defined above,
(7) —C(O)OR$^1$ wherein R$^1$ is defined above,
(8) —C(O)NR$^5$R$^6$ wherein R$^5$ and R$^6$ are defined above,
(9) hydroxyl,
(10) —OR$^1$ wherein R$^1$ is defined above,
(11) —NR$^5$R$^6$ wherein R$^5$ and R$^6$ are defined above, and
(12) —SO$_2$R$^1$ wherein R$^1$ is defined above;
and
A, B, D, and E are independently selected from the group consisting of
(1) hydrogen, and
(2) —C$_1$–C$_6$-alkyl optionally substituted with one or more substituents selected from the group consisting of
(a) —M—R$^{11}$ wherein M is selected from the group consisting of
(i) a covalent bond,
(ii) —C(O)NH—,
(iii) —NHC(O)—,
(iv) —NH—,
(v) —N(CH$_3$)—,
(vi) —O—,
(vii) —S(O)$_n$— wherein n is defined above,
(viii) —C(=NH)NH—,
(ix) —C(O)O—,
(x) —OC(O)—,
(xi) —OC(O)NH—,
(xii) —NHC(O)O—, and
(xiii) —NHC(O)NH—,
and
R$^{11}$ is selected from the group consisting of
(i) —C$_1$–C$_6$-alkyl optionally substituted with a substituent selected from the group consisting of
(1') aryl,
(2') substituted aryl,
(3') heteroaryl, and
(4') substituted heteroaryl,
(ii) aryl,
(iii) substituted aryl,
(iv) heteroaryl,
(v) substituted heteroaryl and
(vi) heterocycloalkyl,
(b) aryl,
(c) substituted aryl,
(d) heteroaryl,
(e) substituted heteroaryl,
(f) heterocycloalkyl,
(g) hydroxy,
(h) —C$_1$–C$_6$-alkoxy,
(i) halo, and
(j) —NR$^{15}$R$^{16}$ wherein R$^{15}$ and R$^{16}$, together with the nitrogen atom to which they are attached, are a 3- to 7-membered ring optionally containing therein a moiety selected from the group consisting of
(i) —O—,
(ii) —NH—,
(iii) —N(C$_1$–C$_6$-alkyl)—,
(iv) —N(C$_1$–C$_6$-alkyl-substituted with aryl)—,
(v) —N(C$_1$–C$_6$-alkyl substituted with substituted aryl)—,
(vi) —N(C$_1$–C$_6$-alkyl substituted with heteroaryl)—,
(vii) —N(C$_1$–C$_6$-alkyl substituted with substituted heteroaryl)—,
(viii) —S—, and
(ix) —S(O)$_q$— wherein q is defined above, or any one pair of substituents selected from the group consisting of AB, AD, AE, BD, BE, and DE, taken together with the atom or atoms to which they are attached, are C$_3$–C$_7$-cycloalkyl or a four- to seven-membered ring containing a moiety selected from the group consisting of
(1) —O—,
(2) —NH—,
(3) —N(C$_1$–C$_6$-alkyl)—,
(4) —N(C$_1$–C$_6$-alkyl substituted with aryl)—,
(5) —N(C$_1$–C$_6$-alkyl substituted with substituted aryl)—,
(6) —N(C$_1$–C$_6$-alkyl substituted with heteroaryl)—,
(7) —N(C$_1$–C$_6$-alkyl substituted with substituted heteroaryl)—, and
(8) —S(O)$_q$— wherein q is defined above, the process comprising (a) reacting a compound of formula (Ia)

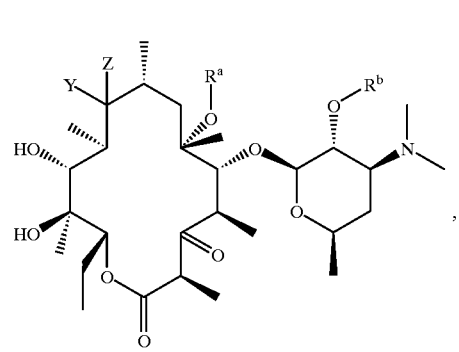

(Ia)

a compound of formula (IIa)

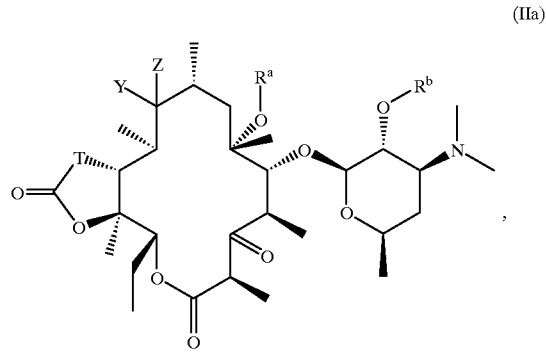

(IIa)

or a compound of formula (IIIa)

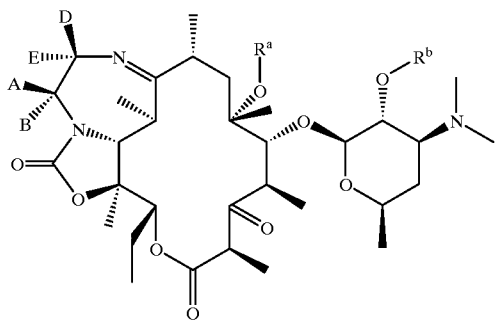

(IIIa)

with an electrophile in the presence of base an oxidizing agent or an iodinating agent, and (b) optionally deprotecting and isolating the desired product.

8. The process according to claim 7 wherein the base is selected from the group consisting of sodium hydride, potassium hydride, potassium carbonate, potassium isopropoxide, potassium tert-butoxide, potassium iso-butoxide, lithium bis(trimethylsilyl)amide, sodium bis(trimethylsilyl)amide, and potassium bis(trimethylsilyl)amide.

9. The process according to claim 7 wherein the electrophile is selected from the group consisting of an alkyl chloride, an alkyl bromide, an alkyl iodide, an alkyl sulfonic anhydride, and an electrophilic nitrogen reagent.

10. The process according to claim 7 wherein the oxidizing agent is a mixture of $OsO_4$, and NMO, $RuO_4$, or m-CPBA and the iodinating agent is selected from the group consisting of a mixture of NIS and water, a mixture of NIA and water, and a mixture of iodine and water.

11. A pharmaceutical composition comprising a therapeutically effective amount of a compound of claim 1 with a pharmaceutically acceptable carrier.

12. A method of treating bacterial infection in a mammal in recognized need of such treatment comprising administering an effective amount of a compound of claim 1.

13. A compound selected from the group consisting of

Compound of formula (II): $R^a$ is $CH_3$, $R^b$ is H, Y and Z together are O, T is —NH—, R is —$CH_2CH$=CH-(phenyl), Compound of formula (II): $R^a$ is $CH_3$, $R^b$ is H, Y and Z together are O, T is —N(W($R^g$))—, W is —$(CH_2)_p$—, p is 4, $R^g$ is phenyl, R is —OH, Compound of formula (II): $R^a$ is —$CH_2CH(OH)CH_2OH$, $R^b$ is H, Y and Z together are O, T is —NH—, R is —OH, Compound of formula (II): $R^a$ is —$CH_2CH$=CH-(3-quinolinyl), $R^b$ is H, Y and Z together are O, T is —NH—, R is —$CH_2CH$=$CH_2$, Compound of formula (II): $R^a$ is —$CH_2CH$=CH-(3-quinolinyl), $R^b$ is H, Y and Z together are O, T is —NH—, R is —$CH_2CO_2C_2H_5$, Compound of formula (III): $R^a$ is $CH_3$, $R^b$ is H, Y and Z together are O, A is —$CH_2OH$, B,D, and E are H, R is —$CH_2$-(4-chlorophenyl), Compound of formula (I): $R^a$ is $CH_3$, $R^b$ is —C(O)$C_6H_5$, Y and Z together are O, R is —OH, Compound of formula (II): $R^a$ is —$CH_2CH$=CH-(3-quinolinyl), $R^b$ is H, Y and Z together are O, T is —NH—, R is —OH, Compound of formula (II): $R^a$ is —$CH_2C$≡CH, $R^b$ is H, Y and Z together are O, T is —NH—, R is —$CH_2CH$=CH-(phenyl), Compound of formula (II): $R^a$ is $CH_3$, $R^b$ is H, Y and Z together are O, T is —N(W($R^g$))—, W is —$(CH_2)_p$—, p is 4, $R^g$ is phenyl, R is —$SO_2CH_3$, Compound of formula (II): $R^a$ is $CH_3$, $R^b$ is H, Y and Z together are O, T is —N(W($R^g$))—, W is —$(CH_2)_p$—, p is 2, $R^g$ is amino, R is —$SO_2CH_3$, Compound of formula (II): $R^a$ is $CH_3$, $R^b$ is H, Y and Z together are O, T is —NH—, R is —$CH_2CH$=$CH_2$, Compound of formula (II): $R^a$ is $CH_3$, $R^b$ is H, Y and Z together are O, T is —NH—, R is —$CH_2CH_3$, Compound of formula (II): $R^a$ is $CH_3$, $R^b$ is H, Y and Z together are O, T is —NH—, R is —$CH_2CO_2CH_3$, Compound of formula (II): $R^a$ is $CH_3$, $R^b$ is H, Y and Z together are O, T is —NH—, R is —$CH_2CH_2CO_2CH_3$, Compound of formula (II): $R^a$ is $CH_3$, $R^b$ is H, Y and Z together are O, T is —NH—, R is —$CH_2C(O)$(phenyl), Compound of formula (II): $R^a$ is $CH_3$, $R^b$ is H, Y and Z together are O, T is —NH—, R is benzyl, Compound of formula (II): $R^a$ is $CH_3$, $R^b$ is H, Y and Z together are O, T is —NH—, R is —$CH_2$-(4-tert-butyl-phenyl), Compound of formula (II): $R^a$ is $CH_3$, $R^b$ is H, Y and Z together are O, T is —NH—, R is —1,1'-biphenyl-2-ylmethyl, Compound of formula (II): $R^a$ is $CH_3$, $R^b$ is H, Y and Z together are O, T is —NH—, R is —$CH_2$-(3-chlorophenyl), Compound of formula (II): $R^a$ is $CH_3$, $R^b$ is H, Y and Z together are O, T is —NH—, R is —$CH_2CH_2CH$=CH-(phenyl), Compound of formula (II): $R^a$ is $CH_3$, $R^b$ is H, Y and Z together are O, T is —NH—, R is —$CH_2$-(3-naphthyl), Compound of formula (II): $R^a$ is $CH_3$, $R^b$ is H, Y and Z together are O, T is —NH—, R is —$CH_2$-(9-anthracenyl), and Compound of formula (II): $R^a$ is $CH_3$, $R^b$ is H, Y and Z together are O, T is —NH—, R is —$CH_2$-(4-fluorophenyl).

* * * * *